(12) United States Patent
Boger et al.

(10) Patent No.: US 9,891,435 B2
(45) Date of Patent: Feb. 13, 2018

(54) APPARATUS, SYSTEMS AND METHODS FOR PROVIDING MOTION TRACKING USING A PERSONAL VIEWING DEVICE

(75) Inventors: Yuval Boger, Pikesville, MD (US); Meir Machlin, Herzliya (IL); Yosef Korakin, Rockville, MD (US)

(73) Assignee: Sensics, Inc., Columbia, MD (US)

( * ) Notice: Subject to any disclaimer, the term of this patent is extended or adjusted under 35 U.S.C. 154(b) by 620 days.

(21) Appl. No.: 13/441,401

(22) Filed: Apr. 6, 2012

(65) Prior Publication Data

US 2012/0262558 A1 Oct. 18, 2012

Related U.S. Application Data

(63) Continuation-in-part of application No. 13/160,314, filed on Jun. 14, 2011, which is a continuation-in-part
(Continued)

(51) Int. Cl.
| | | |
|---|---|---|
| A61B 5/04 | (2006.01) |
| A61B 1/00 | (2006.01) |
| H04N 7/18 | (2006.01) |
| G09G 5/00 | (2006.01) |
| G06F 15/16 | (2006.01) |
| G06F 19/00 | (2011.01) |
| G06F 7/48 | (2006.01) |
| G02B 27/01 | (2006.01) |
| G02B 27/00 | (2006.01) |

(Continued)

(52) U.S. Cl.
CPC ............ *G02B 27/017* (2013.01); *A61B 5/165* (2013.01); *G02B 27/0093* (2013.01); *G06F 3/011* (2013.01); *A61B 5/0476* (2013.01); *A61B 5/11* (2013.01); *G02B 2027/014* (2013.01); *G02B 2027/0138* (2013.01)

(58) Field of Classification Search
CPC .. H04N 7/18; G06F 3/00; G06F 15/16; G06F 19/00; G06F 7/48; A61B 5/04; G09G 5/00
See application file for complete search history.

(56) References Cited

U.S. PATENT DOCUMENTS

| | | |
|---|---|---|
| 4,870,768 A | 10/1989 | Watt et al. |
| 5,581,399 A | 12/1996 | Abe |

(Continued)

FOREIGN PATENT DOCUMENTS

GB 2 376 397 12/2002

OTHER PUBLICATIONS

"Dark Souls" Video Game, Released on Sep. 22, 2011, developed by FromSoftware and published by Namco Bandai Games.*
(Continued)

*Primary Examiner* — Behrooz Senfi
*Assistant Examiner* — Maryam Nasri

(57) ABSTRACT

An apparatus, methods and systems to provide a personal viewing device configured to display an image. The personal viewing device configured to be worn by a user. At least one sensor coupled to the personal viewing device. At least one camera coupled to the personal viewing device and facing outwardly with respect to the personal viewing device. A processor configured for interaction analysis. The processor in communication with the personal viewing device, the at least one sensor and the at least one camera.

17 Claims, 17 Drawing Sheets

Related U.S. Application Data of application No. 11/934,373, filed on Nov. 2, 2007, now abandoned.

(60) Provisional application No. 61/521,634, filed on Aug. 9, 2011, provisional application No. 60/856,021, filed on Nov. 2, 2006, provisional application No. 60/944,853, filed on Jun. 19, 2007, provisional application No. 61/354,909, filed on Jun. 15, 2010, provisional application No. 61/474,643, filed on Apr. 12, 2011, provisional application No. 61/583,573, filed on Jan. 5, 2012.

(51) Int. Cl.

| | | |
|---|---|---|
| *G06F 3/01* | (2006.01) | |
| *A61B 5/16* | (2006.01) | |
| *A61B 5/0476* | (2006.01) | |
| *A61B 5/11* | (2006.01) | |

(56) References Cited

U.S. PATENT DOCUMENTS

| | | | |
|---|---|---|---|
| 5,659,639 | A | 8/1997 | Mahoney et al. |
| 5,708,449 | A | 1/1998 | Heacook et al. |
| 5,796,426 | A | 8/1998 | Gullichsen et al. |
| 5,880,883 | A | 3/1999 | Sudo |
| 5,914,725 | A | 6/1999 | Macinnis et al. |
| 5,956,431 | A | 9/1999 | Iourcha et al. |
| 6,166,744 | A | 12/2000 | Jaszlics et al. |
| 6,467,913 | B1 | 10/2002 | Holden et al. |
| 6,529,331 | B2 | 3/2003 | Massof et al. |
| 6,826,532 | B1 | 11/2004 | Casby et al. |
| 7,061,674 | B2 | 6/2006 | Mogamiya |
| 7,512,902 | B2 | 3/2009 | Robertson et al. |
| 7,817,167 | B2 | 10/2010 | Suzuki et al. |
| 7,969,383 | B2 | 6/2011 | Eberl et al. |
| 8,004,492 | B2 | 8/2011 | Kramer et al. |
| 8,046,719 | B2 | 10/2011 | Skeurup et al. |
| 8,085,902 | B2 | 12/2011 | Bonfiglio et al. |
| 8,099,668 | B2 | 1/2012 | Garbow et al. |
| 2001/0012011 | A1* | 8/2001 | Leavy .................. G06F 3/012 |
| | | | 345/419 |
| 2002/0090985 | A1* | 7/2002 | Tochner .................. A63F 13/12 |
| | | | 463/1 |
| 2002/0181115 | A1 | 12/2002 | Massof et al. |
| 2003/0043268 | A1 | 3/2003 | Mann |
| 2005/0078378 | A1 | 4/2005 | Geist |
| 2005/0207031 | A1 | 9/2005 | Eckhardt et al. |
| 2005/0245302 | A1 | 11/2005 | Bathiche et al. |
| 2006/0009702 | A1* | 1/2006 | Iwaki et al. .................. 600/520 |
| 2006/0061555 | A1 | 3/2006 | Mullen |
| 2007/0120974 | A1 | 5/2007 | Chen |
| 2008/0094417 | A1* | 4/2008 | Cohen .................. A63F 13/10 |
| | | | 345/632 |
| 2008/0106489 | A1 | 5/2008 | Brown et al. |
| 2009/0059364 | A1 | 3/2009 | Brown et al. |
| 2010/0110368 | A1 | 5/2010 | Chaum |
| 2010/0159434 | A1* | 6/2010 | Lampotang .............. G09B 9/00 |
| | | | 434/365 |
| 2010/0182340 | A1 | 7/2010 | Bachelder et al. |
| 2011/0241976 | A1 | 10/2011 | Boger et al. |
| 2012/0113223 | A1* | 5/2012 | Hilliges et al. .................. 348/46 |

OTHER PUBLICATIONS

Office Action for U.S. Appl. No. 12/263,711, dated Dec. 23, 2011.
Office Action for U.S. Appl. No. 11/934,373, dated Jul. 1, 2011.
Office Action for U.S. Appl. No. 11/934,373, dated Feb. 9, 2011.
Murphy et al., "MSSMP: No Place to Hide," Report: Naval Command Control and Ocean Surveillance Center, Published Jun. 1997 [retrieved on Aug. 11, 2008]. Retrieved from the Internet: <URL: http://www.spawarnavy.mil/sti/publications/reprints/robotics/rr18.pdf>.
Citation containing publication date for: Murphy et al., "MSSMP: No Place to Hide," Report: Naval Command Control and Ocean Surveillance Center, Published Jun. 1997 [retrieved on Aug. 11, 2008]. Retrieved from the Internet: <URL: http://www.stormingmedia.us/87/8742/A874224.html>.
International Search Report for International Application No. PCT/US2011/040438, dated Mar. 28, 2012.
International Search Report and Written Opinion for International Application No. PCT/US2007/083500, dated Aug. 18, 2008.
International Search Report and Written Opinion for International Application No. PCT/US12/33185, dated Jul. 18, 2012.
Extended European Search Report dated May 4, 2015 for European Application No. 12771791.6-1553.

* cited by examiner

FPGA to REQUESTOR data transfers

The width of the bus from the FPGA to the REQUESTOR is 32 bit.

| 31 | | | | | | | | 23 | | | | | | | | 15 | | | | | | | | 7 | | | | | | | 0 |

Data transfer is implemented through a FIFO

Specific message formats are as follows:

1. Raw Image Transfer

| 0 | 0 | x | x | x | x | x | x | Red (0:255) | | | | | | | | Green (0:255) | | | | | | | | Blue (0:255) | | | | | | | |
| 31 | | | | | | | | 23 | | | | | | | | 15 | | | | | | | | 7 | | | | | | | 0 |

2. Run-Length Encoding Transfer

| 0 | 1 | Starting row (0:239) | | | | | | | | Starting Column (0:319) | | | | | | | | Run Length (1:320) | | | | | | | | | | | | | |
| 31 | | | | | | | | 23 | | | | | | | | 15 | | | | | | | | 7 | | | | | | | 0 |

3. 2D Histogram

| 1 | 0 | Histogram Index | | | | | | | | | | | | x | x | Histogram Value | | | | | | | | | | | | | | | |
| 31 | | | | | | | | 23 | | | | | | | | 15 | | | | | | | | 7 | | | | | | | 0 |

4. Special Messages
End of Frame

Sent to REQUESTOR at the end of every image frame

| 1 | 1 | x | x | x | x | x | x | x | x | x | x | x | x | x | x | x | x | x | x | x | x | x | x | 0 | 0 | 0 | 0 | 0 | 0 | 0 | 1 |
| 31 | | | | | | | | 23 | | | | | | | | 15 | | | | | | | | 7 | | | | | | | 0 |

Fig. 5c

Commands from REQUESTOR to FPGA

Width of REQUESTOR to FPGA commands is 16 bits

| 15 | | | | | | | 7 | | | | | | | | 0 |
|----|--|--|--|--|--|--|---|--|--|--|--|--|--|--|---|

Commands are:

1. Clear FIFO

| 0 | 0 | 0 | 1 | x | x | x | x | x | x | x | x | x | x | x | x |
|---|---|---|---|---|---|---|---|---|---|---|---|---|---|---|---|
| 15 | | | | | | | 7 | | | | | | | | 0 |

2. Set data transfer mode

Format:

| 0 | 0 | 1 | 0 | x | x | x | x | x | x | x | x | x | A | B | C |
|---|---|---|---|---|---|---|---|---|---|---|---|---|---|---|---|
| 15 | | | | | | | 7 | | | | | | | | 0 |

Where:

A: 1 if RGB image is to be transferred; 0 if not

B: 1 if 2D histogram is to be transferred at the end of each frame; 0 if not

C: 1 if RLE data is to be transferred; 0 if not

Valid modes:

| A | B | C |
|---|---|---|
| 1 | 0 | 0 |
| 1 | 1 | 0 |
| 0 | 1 | 0 |
| 0 | 1 | 1 |
| 0 | 0 | 1 |

The command goes into effect at the next end of frame

Fig. 5d

3. Set threshold logic

| 0 | 0 | 1 | 1 | Band | Track | x | x | x | x | $L_{high}$ | $L_{low}$ | $A^*_{high}$ | $A^*_{low}$ | $B^*_{high}$ | $B^*_{low}$ |
|---|---|---|---|------|-------|---|---|---|---|------------|-----------|--------------|--------------|--------------|--------------|
| 15 |  |  |  |  |  |  |  | 7 |  |  |  |  |  |  | 0 |

Band is 0 or 1 for the two bands tracked by each FPGA.

Track is 1 if tracking for this particular band is enabled, 0 if not.

Where the $L_{high}$ is 1 if the high threshold is enabled for L, 0 if not enabled. Same for the other flags.

4. Set threshold value

This commands sets the specific percentile for each threshold

| 0 | 1 | 0 | 0 | Band | Param | Value |  |  |  |  |  |
|---|---|---|---|------|-------|-------|--|--|--|--|--|
| 15 |  |  |  |  |  | 7 |  |  |  |  | 0 |

Band is 0 or 1 for the two bands tracked by each FPGA.

Param is:

| Param | Meaning |
|-------|---------|
| 0 | $B^*_{low}$ |
| 1 | $B^*_{high}$ |
| 2 | $A^*_{low}$ |
| 3 | $A^*_{high}$ |
| 4 | $L_{low}$ |
| 5 | $L_{high}$ |

Value is 0:100 for percentile

Fig. 5e

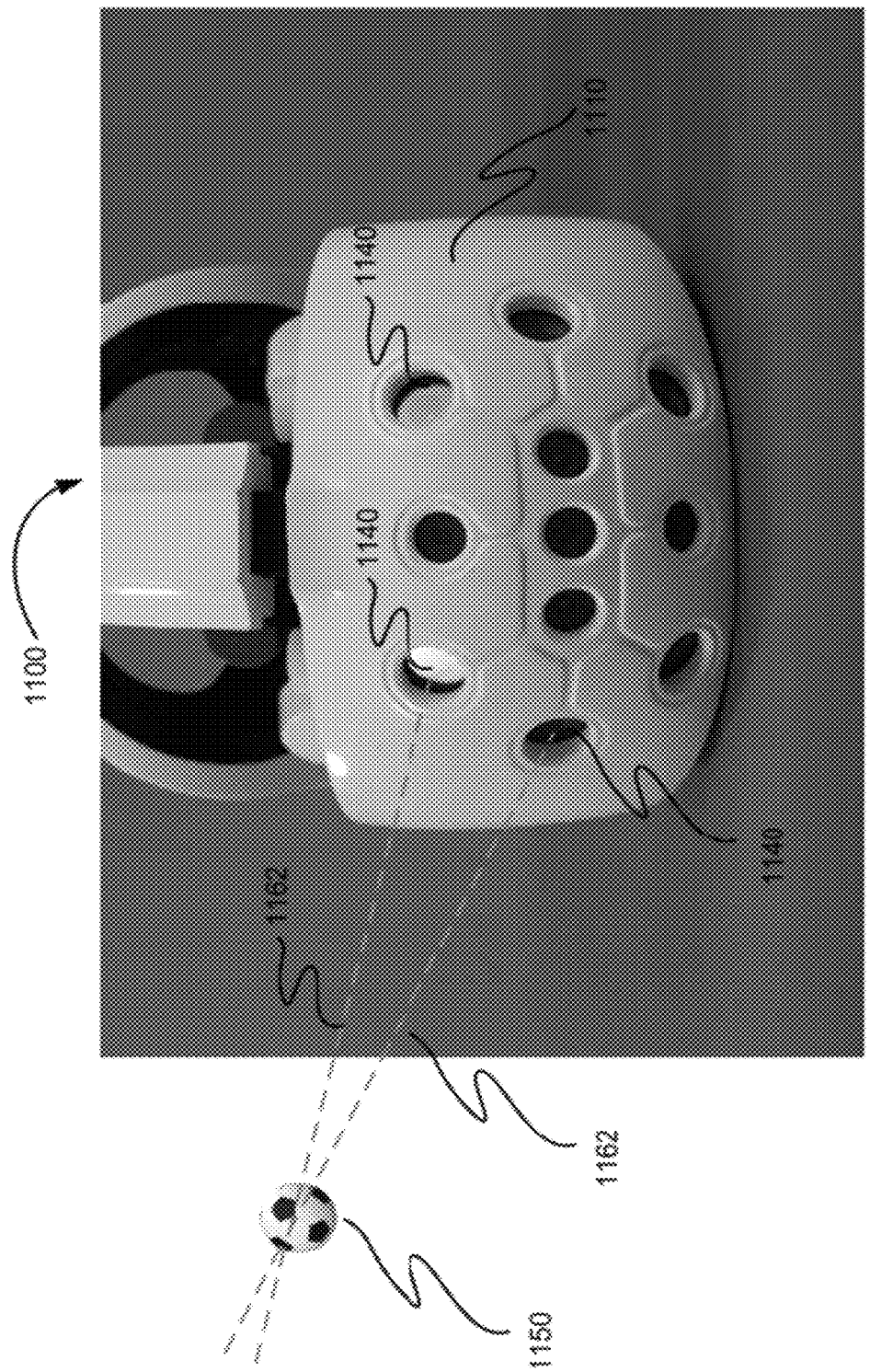

APPARATUS, SYSTEMS AND METHODS FOR PROVIDING MOTION TRACKING USING A PERSONAL VIEWING DEVICE

CROSS-REFERENCE TO RELATED APPLICATIONS

This application is a continuation-in-part of pending U.S. patent application No. 13/160,314, filed Jun. 14, 2011, entitled "Systems and Methods for Personal Viewing Devices" (the '314 application) and this application also claims priority to and benefit of U.S. Provisional Patent Application No. 61/521,634, filed Aug. 9, 2011, entitled "Systems and Methods for Providing Motion Tracking Using Personal Viewing Device" each of which is herein incorporated by reference in its entirety. The '314 application is a continuation-in-part of pending U.S. patent application Ser. No. 11/934,373, filed Nov. 2, 2007, entitled "Systems and Methods for a Head-Mounted Display," which claims priority to and the benefit of U.S. Provisional Patent Application Ser. No. 60/856,021, filed Nov. 02, 2006, entitled "Visual Head Mounted Display Device" and U.S. Provisional Patent Application Serial No. 60/944,853, filed Jun. 19, 2007, entitled "Systems and Methods for a Head-Mounted Display" each of which is herein incorporated by reference in its entirety. The '314 application also claims priority to and the benefit of U.S. Provisional Patent Application No. 61/354,909, filed Jun. 15, 2010, entitled "Systems and Methods for Personal Viewing Devices" and U.S. Provisional Application No. 61/474,643 filed on Apr. 12, 2011, entitled "Systems and Methods For A Head Mounted Display that Includes an Onboard Processor" each of which is herein incorporated by reference in its entirety. This application also claims priority to and benefit of U.S. Provisional Patent Application No. 61/583,573, filed Jan. 5, 2012, entitled "Systems and Methods for Providing Enhanced Motion Tracking Using a Personal Viewing Device."

BACKGROUND

Applications (e.g., video games, maintenance simulators) operating on head mounted displays (HMDs) or personal viewing devices can include motion sensing to determine orientation of a character, a person or object within an environment. Different approaches for motion sensing exist. One approach is active tracking (e.g., inertial tracking), which involves placing a powered sensor (or sensors) on the object to be tracked and then processing the sensor readings either in or near the sensor.

Another possible approach is optical tracking, in which cameras are placed in the surrounding environment and targets are placed on the objects (e.g., head/arms/simulated weapon) to be tracked. In some embodiments, these cameras can emit a light from a light source (e.g., a coded light) to assist with the identification and location of the targets. The information received from the cameras is then extracted.

Disadvantages exist when implementing the approaches discussed above. For example, cameras being placed in the area surrounding the person or object being tracked can introduce latency into the system due to lead time associated with the start of actual tracking and also limits the size and place in which tracking can occur. The above approaches can track objects only when they are in a particular location (e.g., a person's hands cannot be tracked when the person is behind an obstruction (e.g., a sofa in a living room). The above-described approaches also often do not work in an outdoor environment with bright sunlight. The above approaches also often require installation and sometimes calibration of external sensors in fixed and known points in an environment. The above-described approaches also do not track movement from the view point of the user's head and eyes. In virtual reality and augmented reality applications, the position of the object/weapon/hand relative to the eyes/head can be more relevant to the displayed image environment than an absolute position relative to some fixed reference point.

Accordingly, a need exists for methods, systems and apparatus than can accomplish motion tracking from the point of view of a user's head and eyes and that facilitate the user's interaction with an environment (virtual or augmented) presented to the user. Another need also exits for virtual and augmented reality related methods, systems and apparatus applications that facilitate a 360 degree (e.g. fully spherical) tracking area as well as a limitless tracking area. Another need also exists for virtual and augmented reality related methods, systems and apparatus applications that can track both the orientation and position of an object or person.

SUMMARY

In one embodiment an apparatus includes a personal viewing device configured to display an image. The personal viewing device is configured to be worn by a user. At least one sensor is coupled to the personal viewing device. At least one camera is coupled to the personal viewing device and faces outwardly with respect to the personal viewing device. A processor is configured for interaction analysis, the processor being in communication with the personal viewing device, the at least one sensor and the at least one camera.

In some embodiments a non-transitory processor-readable medium storing code representing instructions to be executed by a processor is disclosed. The code includes code to cause the processor to receive data from at least one outward-facing camera coupled to a personal viewing device. The personal viewing device is configured to be coupled to a user (e.g., via head-mounted goggles). The code further includes code to receive data from at least one sensor coupled to the personal viewing device and display a plurality of images based on the data received from the at least one camera and the at least one sensor.

A system includes a motion capture module configured to receive data associated with images captured by at least one outward-facing camera coupled to a personal viewing device. A sensor data capture module is configured to receive sensor data associated with at least one sensor coupled to the personal viewing device. An image analysis module is configured to communicate with the motion capture module to coordinate a display of images based on the data received by the motion capture module.

BRIEF DESCRIPTION OF THE DRAWINGS

FIG. 5c illustrates an example of formatting data using a real time target tracking implementation in accordance with embodiments.

FIGS. 5d-5e include an example of commands that can be sent to a real time target tracking implementation in accordance with embodiments.

FIG. 11 illustrates object triangulation in accordance with various embodiments.

DETAILED DESCRIPTION

Figure 1A:
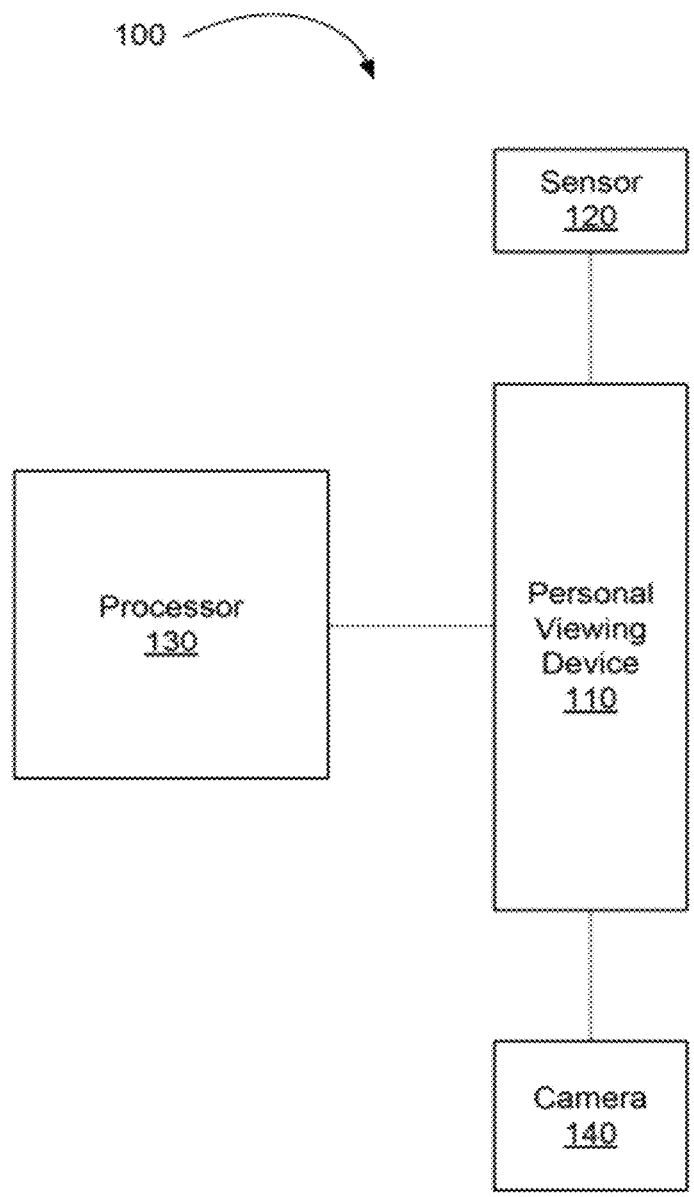
FIG. 1a is schematic diagram of an apparatus/system in accordance with embodiments.

Embodiments relate to apparatus, systems and methods for providing motion tracking and a user interface using a personal viewing device, such as, for example, a head mounted display, head mounted virtual reality goggles, and/or virtual reality glasses. More particularly, embodiments relate to apparatus, systems and methods for using one or more cameras and optional sensors placed on a head mounted display to track and interact with a body part, an object, or one or more passive markers, placed on an object or body part to be tracked.

In some embodiments, the term "object," as used herein, refers to one or more body parts.

A personal viewing device is a device for displaying information to one or both eyes through a lens. The lens is used so the personal viewing device can be located in front of and near one or both eyes of the wearer. The lens can be used to focus an image from a display directly on an eye or the lens can be a lens of a projector that focuses the image on a reflective surface so that it is visible to the eye. A personal viewing device can include, but is not limited to, a monocular or binocular head mounted display (HMD), head mounted goggles (HMG), an augmented reality device, virtual reality glasses, a scope simulator, a monocular simulator, a binoculars simulator, or a telescope simulator. A scope simulator, for example, is essentially a monocular version of a personal viewing device that is mounted on a gun rather than a head. A personal viewing device can include monocular or binocular displays positioned in front of one or both eyes. One or more displays of a personal viewing device have been driven by an external image generating device, such as a computer or video player through a wired or wireless connection. Various embodiments may be coupled to eyeglasses, sunglasses, and or a user (e.g. the head, an arm, and/or somewhere else on a user's body). In some embodiments, the image generating device is coupled directly to the head mounted display.

A personal viewing device can be configured in number of ways. One configuration is the fully immersive configuration. In this configuration, the user only sees data that is generated for the personal viewing device. This data can be displayed on the displays of the personal viewing device or outside of the personal viewing device.

Another configuration is the optical see-through configuration. In this configuration, the personal viewing device includes a see-through glass or plastic lens and perhaps an optical mirror or other reflective optical element. Graphics and/or images are overlaid on the see-through glass or plastic lens. In some embodiments, the personal viewing device acts as a heads-up display.

Another configuration is the video see-through configuration. In this configuration, one or more cameras are mounted on the personal viewing device or near the personal viewing device. A video signal from the one or more cameras is then presented inside the personal viewing device together with other information producing what is sometimes referred to as "mixed reality" and/or "augmented reality." In a mixed reality environment, information generated and seen inside the personal viewing device is mixed with information obtained outside of the personal viewing device to create one combined virtual environment.

In various embodiments, motion tracking is provided using a camera or a set of cameras placed on or around a user's head and may include passive markers (such as colored rubber bands or reflective markers) placed on the objects to be tracked. The cameras are positioned such that they are outwardly-facing (i.e., aimed away from the head of the wearer of the device). Such a system maximizes the motion tracking area and allows a user to move freely. Such a system tracks motion from the point of view of the user of the personal viewing device.

Various embodiments, can implement a "rear view" or "side view" camera where a live camera image from a camera pointing to a direction not normally within the field of vision, of the user, is provided to the user. In some embodiments, the various cameras can be configured to sense relative position of, for example, a wearer's arm/hands and not to display an image of the user's arm. For example, the camera may sense a position of a user's arm positioned next to or behind the user's head in a position where the arm would not normally be visible.

Various embodiments can allow for tracking the user's position inside a room, for instance, by determining the distance and direction of known objects that are fixed in that room.

In various embodiments sensors and/or cameras are attached to traditional eyewear or other apparatus without user display screens, (e.g., sunglasses, eyeglass, hats, wrist devices and/or the like). These sensors and/or cameras can then and provide sensing data to a connected device such as a processor, phone, computer, gaming device, etc.

FIG. 1a is a schematic diagram of an apparatus 100, which can also be implemented as a system, in accordance with an embodiment. It should be noted that though FIG. 1a depicts an apparatus 100, embodiments may be implemented as a system of one or more modules in communication with each other. Included is a personal viewing device 110 configured to display an image. Embodiments of the apparatus are configured to be worn by a user. One or more sensors 120 are coupled to the personal viewing device 110. One or more cameras 140 are coupled to the personal viewing device 110 and face outwardly with respect to the personal viewing device 110. One or more processors 130 configured for interaction analysis are operatively coupled to and in communication with the personal viewing device 110, the one or more sensors 120, and the one or more cameras 140.

Figure 1B:
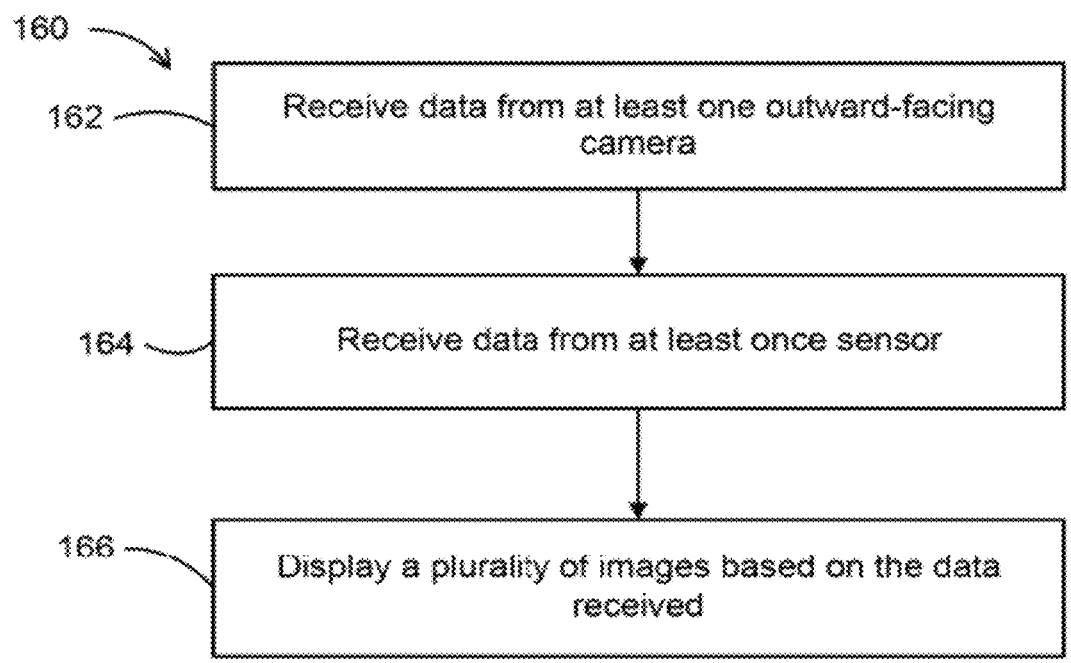
FIG. 1b is a flowchart of a method for interaction analysis in accordance with embodiments.

FIG. 1b is a flow chart of a method 160 for interaction analysis in accordance with an embodiment. The method 160 includes receiving data from at least one outward-facing camera coupled to a personal viewing device at 162. The personal viewing device configured to be coupled to a user. The method further includes receiving data from at least one sensor coupled to the personal viewing device at 164. A plurality of images based on the data received from the at least one camera and the at least one sensor are displayed at 166.

Figure 2:
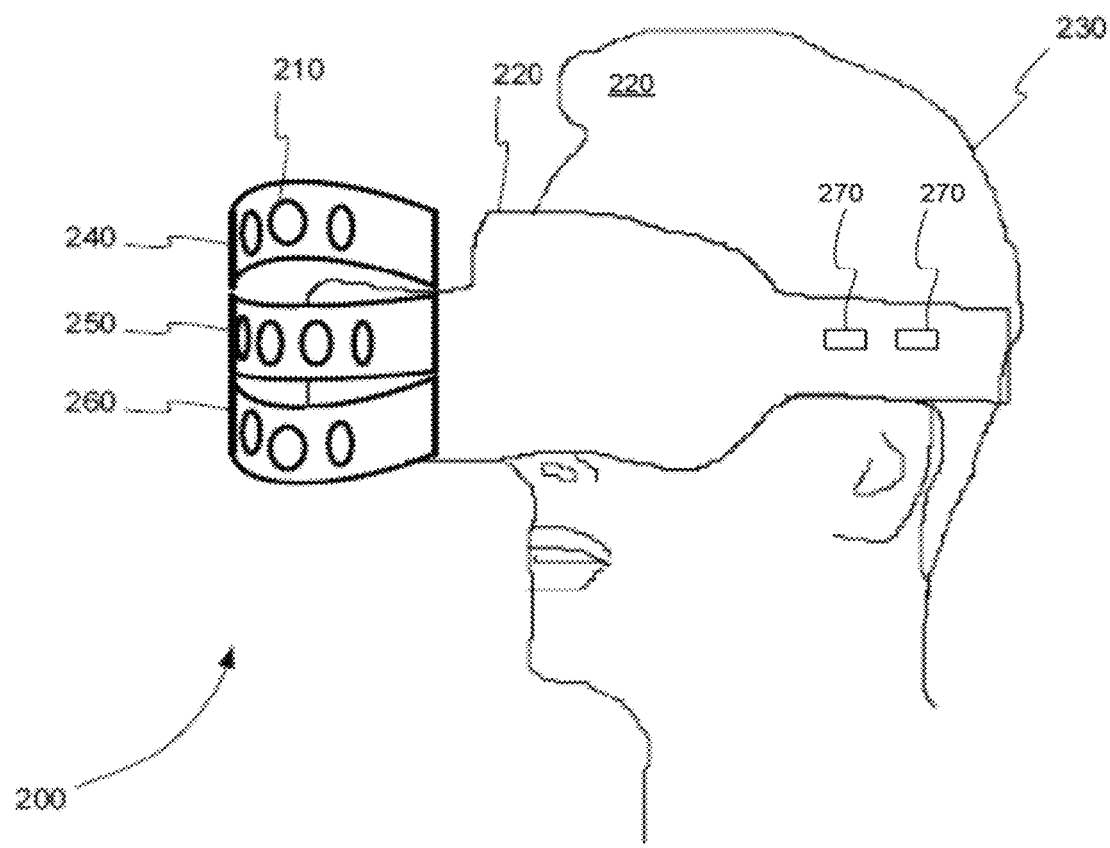
FIG. 2 is a schematic diagram of a system in accordance with embodiments.

FIG. 2 is a schematic diagram of a system 200 that includes ten outwardly facing cameras 210 placed on a personal viewing device 220 to provide, in part, motion tracking of, for example, passive markers (420, shown in FIG. 4) placed on an object (410, shown in FIG. 4), in accordance with various embodiments. In various embodiments the cameras 210 can also be used to provide motion tracking of objects that do not have passive markers attached thereon. The outward facing cameras 210 can be mounted on a head mounted display, such as a personal viewing device 220, around a user's head 230, where the cameras are pointing "outward" (i.e., out away from the head 230). The cameras 210 can be connected to a set of processors, processing boards or electronics (not shown), which can be collectively referred to as a processor, that is carried on the user or coupled directly to the viewing device 220. The processor can include the processing system of FIG. 10, for example. In some embodiments, the processor is disposed within the personal viewing device 220. Alternatively, the processor can be attached to the user's body, such as with a belt clip, bag, harness, etc., for example. Alternatively, the processor can be placed away from the user's body and information from the cameras can be transmitted wirelessly to the processor and back to receiving modules of the personal viewing device 220. Though the depicted embodiment uses ten outwardly facing cameras 210, one or more cameras may be used in various embodiments. In some embodiments, one or more of the cameras (regardless of type) can be used for motion sensing, image capture, and/or both.

In various embodiments, the processor can operate in a number of different modes that can either function independently or in combination. For example, the processor can simply pass through an external video signal to the personal viewing device 220.

In another mode, the processor can execute an application and generate its own modified video signal based on the information received from various cameras and/or sensors. In some embodiments a portion of an image, based on the data received from various cameras and/or sensors can be displayed. The application can be a simulation, a game, a business application, or a combination thereof. The application can be downloaded from the Internet using a wired or wireless connection. The application can be part of an online marketplace for applications for personal viewing devices. In some embodiments, the application can be hard-coded into the processor.

In another mode, the processor can generate a second image for display to the user. For example, the video signal from an external source can be replaced, modified, or overlaid with graphics, symbols, or video that is generated and/or supplied by the processor.

In another mode, the processor can analyze images from a camera or cameras attached to the viewing device. The processor can, for example, identify targets or objects and optionally present this identification for the user. The processor can enhance the image received from the camera so as to improve the visibility, to improve the contrast or highlight specific areas of the image, for example. In some embodiments, the image displayed to the user can be a representation of the object, but not necessarily an actual image of the object. In other words, the camera can capture an image of a user's hand, but the displayed image can represent the user's hand as a robot hand, pointer, or other such image.

The processor can, for example, use camera or cameras attached to viewing device 220 to determine the location, orientation, speed, and acceleration of the user, or to determine the location, orientation, speed and acceleration or various body parts of the user or of other visible objects. The representation of the body part or other visible object can include an actual image or other representation as described above.

In various embodiments, the personal viewing device 220 allows for applications to communicate between two or more personal viewing devices. This communication can be wired or wireless. Wireless communication can include, but is not limited to, Wi-Fi, Bluetooth, 3G, or 4G communication. Communications can be in 'peer to peer' mode or can be routed through a central hub, server or communications gateway. Applications that provide communication between two or more personal viewing devices can include a multi-player game, for example, in which the multiple users operate in the same or similar virtual or augmented environment.

Various embodiments can also include one or more sensors 270 that are mounted on personal viewing device 220. The sensors 270 can be any type of sensor or combinations thereof. Examples of sensors include GPS, Local Positioning System (LPS), altimeters, which can identify where the user is located in a space; motion sensors (e.g., accelerometers), which can generate data associated with the orientation of the user's head or if the user is moving in a specific direction, e.g., by walking, running or jumping. The sensors 270 can be used to in part determine the location of the user and the angle of and position of the user's head. This information can then be used to select what images are presented to the user and how they are oriented. For example, if the user is in a room with their head aimed upward, the system can figure out which room they are located in and present a representation of the ceiling of that room. Other types of sensors can include biometric sensors that can sense the user's heart rate, temperature, brain wave activity, perspiration or other biometric sensors.

Such sensors can, for example, allow for sensing of the stress level of a user and can adjust simulation accordingly. For example in the case of a game, if a user is relaxed the action level of the simulation and increase the difficulty or complexity of the simulation (e.g., number of obstacles to overcome, enemies to be destroyed, etc.). If a user is dangerously stressed, in some embodiments, the simulation might decide to stop altogether to protect the health of the user. In embodiments that include brain wave activity sensors, a user can interact with the system using their brain activity. For example, certain types of sensed brain activity can be indicative of a user's "engagement" with the simulation. Based on such sensed activity the simulation can be modified accordingly. In some embodiments, the engagement with a particular type of simulation can be stored by the processor to make future recommendations of simulations that may be of interest to the user. Such recommendations can also be made based on input from these and other sensors.

Other sensors include thermal sensors (to determine, for example, temperature of the personal viewing device, the user's body, the external environment, etc.), a moisture sensor (to determine, for example, moisture in the external environment or on the user), a pressure sensor (to determine, for example, pressure applied to an object, the viewing device, the user, etc.), a light sensor or an audio sensor.

Various embodiments can include eye tracking and blink detection sensors that can track where a user is directing their gaze and when the user blinks. Such information can be used, for example, to select and interact with something the user is looking at within the display. For example, various embodiments can use such eye tracking and blink detection information/interaction for a hands-free mode of operation; for instance, when the user's hands are occupied with some other activity or in the case of a person with disabilities.

Various embodiments can use sensor fusion to combine data from two or more sensors to produce enhanced information that could otherwise not be produced. For example, data from a user heart rate sensor and user temperature sensor could be combined to ascertain a user's stress level.

FIG. 2 illustrates an example of a device including ten cameras 210, in accordance with embodiments, that are positioned in three rows. There are three cameras in the top row 240, four cameras in the middle row 250, and three cameras in bottom row 260. Each of the cameras 210 is pointed in a different direction, outward from the user, to maximize the tracking area. The field of view of each camera 210 may or may not overlap with the field of view of another camera.

The cameras 210 are shown positioned in front of user's head 230. In various embodiments, however, one or more outwardly facing cameras 210 can be placed anywhere around a user's head 230 and capture images/motion in multiple other directions.

Various embodiments can integrate user coordinates with real world coordinates into virtual and/or augmented reality applications. User coordinates and real world coordinates can be explained by reference to the following example. In general, user coordinates are defined using a coordinate system that can be relative to the position and/or orientation of the user's body, or somewhere thereon. For example, a user wearing a HMD could be sitting on a swivel chair holding a cup in their hand where the hand is not moving. Relative to their left shoulder, the cup is two feet in front of their shoulder (e.g., two feet in a direction perpendicular to the line connecting both of their shoulders) and one foot to the right of their left shoulder. The cup's position has just been described using an example of user coordinates, e.g., using a coordinate system that is relative to the position and/or orientation of the user's body, in this case the relative to the user's left shoulder. If the user were to turn in the swivel chair, the cup could remain in the same coordinates relative to the user's body (e.g., two feet out front, one foot to the right). The position of that same cup can also be measured in real world coordinates, e.g., a coordinate system fixed to something other than the user's body; for example, the coordinate system could be fixed relative to the room in which the user is positioned. The position of the cup can be some (X, Y, Z) coordinate within in the room. In this case, when the user rotates in their swivel chair, the coordinates of the cup move in the real world coordinate system, however remain still in the user coordinate system.

Some embodiments can optionally use both user coordinates and real world coordinates simultaneously. For example, an application might want to know if the user's hand is in front of their face or behind their body. The application could use user coordinates to determine the position of the user's hand. An application might also want to know whether the user is close to a bottle on a desk and use real world coordinates to calculate the answer.

Various embodiments can use data from both cameras and sensors to help position objects with respect to user coordinates, real world coordinates or both. For example, because the cameras of the apparatus rotate with the user as they move their head, data from cameras can be used to calculate the position of objects in user coordinates. Data from sensors can be used to calculate the user's exact position and orientation in a room, which can then, for example, be used to transform the user coordinates into real world coordinates.

In various embodiments, motion tracking is provided using image recognition and tracking software and algorithms that analyze the images and data received from the set of cameras placed around a user's head. Various embodiments can also use image recognition software and algorithms to identify objects that are imaged by one or more of the outward looking cameras 210. In some embodiments, the use of the passive markers is optional. For example, a person's hand and/or fingers, without any markers placed thereon, could be brought into the field of view of one of the cameras 210. The camera recognizes the hand and/or fingers and responds appropriately. For example, a representation of the hand and/or fingers could be displayed on the personal viewing device 220 allowing the user to interact with other components being displayed by manipulating their actual hand and/or fingers. The user could be presented with a virtual ball on their personal viewing device. The user could then reach out with their real hand to where he perceives the ball is, close his hand as if to grab the ball and then bring his real hand back and motion as if throwing the ball. The cameras 210 would capture images of the user's hand, analyze the images and recognize the user was grabbing the ball and throwing it in a particular direction. As this was happening, the apparatus could present the user with images that represent the hand grabbing the ball, throwing it and then images of the ball flying through the air in the appropriate direction. Embodiments could also calculate the acceleration of the user's actual hand to calculate the trajectory the ball will take in the virtual environment. Such calculations can be made using data received and/or derived from the images or from an accelerometer or from a combination thereof. The apparatus would then show the ball flying through the air and landing in a position at a distance dictated by how hard/fast and at what angle the user had "thrown" the virtual ball. Various embodiments can also use motion tracking of the fingers to recognize gestures made therewith. For example, a "thumbs up" gesture may signify approval of a particular option presented by the application. As another example, a pinch gesture (e.g., where the thumb and index finger are brought together) can be used to signify picking up a virtual object.

Various embodiments can also allow the user to interact with unknown and/or unexpected objects (marked or unmarked) that might come into the field of view of an outward facing camera. For example, a physical beverage bottle could have been placed on a physical table located in a room. A user playing a virtual/augmented reality game and wearing the device might walk into the real room, where the camera could capture and recognize that there was a table with a bottle placed thereon. The camera could further sense and recognize the beverage bottle to be a cola bottle (e.g., by identifying and scanning the UPC symbol on the bottle and searching a database of products or based on the shape of the object) and place a representation of it into the display. The user could walk over to the bottle and grasp it with their physical hand and physically drink the real contents inside; as this is happening the display would show representations of the user's hand and bottle with its contents being emptied. The device could, for example, recognize that the user is drinking the contents of the bottle and increase the user's health level within the game.

In various embodiments, the outward facing cameras could "pass through" the images being captured by the outward facing camera directly to the user. As the user moves around, the camera could recognize items with which a user can interact, such as the beverage bottle in the above example. If the user decided to interact with the item, the combination of sensors, cameras and integrated processor can discern how the user is interacting with the item and respond accordingly. For example the user might decide to grab the bottle and attempt to throw it into a waste receptacle that is being displayed to the user. The device could recognize the waste receptacle, and if the user is able to successfully get the bottle into the receptacle the interaction would respond accordingly. The user might, on the other hand, decide to drink the contents of the bottle. The device could recognize that this was the case using, for example, visual cues garnered from the captured images, accelerometers calculating head tilt angle and/or combinations thereof. The device can also use visual or other cues to recognize that only a portion of the contents of the bottle were consumed.

Various embodiments can also include haptic feedback mechanisms built into the personal viewing device. In such an embodiment, the system could use information received and/or derived from the captured images to recognize that an object was thrown at a person. For example, the device could use information to identify the projectile, e.g., a ball shaped or a bullet shaped sponge. This information would be combined with information from the haptic feedback device(s), which could indicate with how much force the projectile hit the user. The device could then, for example, subtract points from the user in a game environment based on the type of projectile and how hard the user was hit. For example, the device could subtract more points for a hit from a sponge bullet then for a hit from a sponge ball, though they both might have impacted the user with the same force.

Various embodiments can use a GPS device, local positioning device, visual image cues or combinations thereof to calculate the location of the user. The GPS and local positioning device can be mounted onto a personal viewing device and the image cues can be received and/or derived from outward facing cameras. For example, the device might be able to identify a placard on a door and garner that the room is a utility closet. This information can be combined with GPS and/or local positioning information to calculate that the user is about to enter a utility closet located on a particular floor of a building in a particular location. The device can then present the user with images that are appropriate for the location. For example, if within a virtual reality game the utility closet is to represent a jail cell, the user could be presented with an image of a door comprising of bars, instead the solid door that is actually in front of the user. However, the door to the utility closet on the fourth floor of the building might be restricted, and in that case the user might not even be presented with an image of a door at all, if he were to go past the room.

In various embodiments, the information from a GPS device can be combined with information from other position sensors. For example, the GPS device can provide coarse position data signifying that the user is in a room; whereas, other position sensors can provide fine position data inside that room. In various embodiments, a GPS device and other position sensors can be used instead of one another. For example, when the user is outdoors and there is valid GPS signal, the GPS device might provide the location; whereas when the user is indoors, in an area without valid GPS signal, other position sensors (e.g., Wi-Fi based positions sensors) can provide location instead of the GPS device.

In various embodiments cameras can also be used to automatically identify and analyze movement relative to walls and/or other fixed objects, record a surrounding video of the person, identify motion, and recognize faces or gestures. For example, the faces of nearby people may be captured and recognized, their names could then appear on the display.

In various embodiments, multiple cameras provide a wider tracking field of view than might be obtained with a single camera. Each camera acts as a separate tracking device. As a result, an object can be tracked continuously from the field of view of one camera to the field of view of another camera, essentially widening the field of view. In some embodiments, cameras are positioned around the entire perimeter of the device such that a 360 degree field of view is obtained. In some embodiments, information from multiple cameras can be used to determine the precise position, in space, of a tracked object. Additionally, sensors, such as audible sensors, can be placed around the perimeter of the device such that position, directionality and magnitude of signals can be perceived.

Various embodiments can implement algorithms consolidate information from multiple cameras or sensors so as to, for example, increase the sensing accuracy and/or provide predictive tracking. By way of example, if a tracked object is obstructed for a short period of time, the embodiment could provide an approximate location for that object until it is sensed again.

In various embodiments cameras can include, however are not limited to, high-definition cameras, infrared cameras, thermal imaging cameras, camera's configured to capture energy from various bands of the Electro-magnetic spectrum (e.g., visible light, ultra violet, X-ray, gamma, and/or the like).

In various embodiments, an outward facing camera or cameras can be used for video recording. A user can, for example, record an area of up to 360 degrees of view as they are walking through the area. Such a system can be used for an architectural walkthrough or an extreme sports experience, for example. Additionally a 3D reconstruction could be performed by combining the video from the various cameras and position/location sensors.

In various embodiments, outward facing cameras can be used for collision avoidance. The cameras can be used to prevent a user from inadvertently hitting an object (e.g., a table or wall) while playing a game or to notify a user if another game player is approaching from behind, for example.

Figure 3:
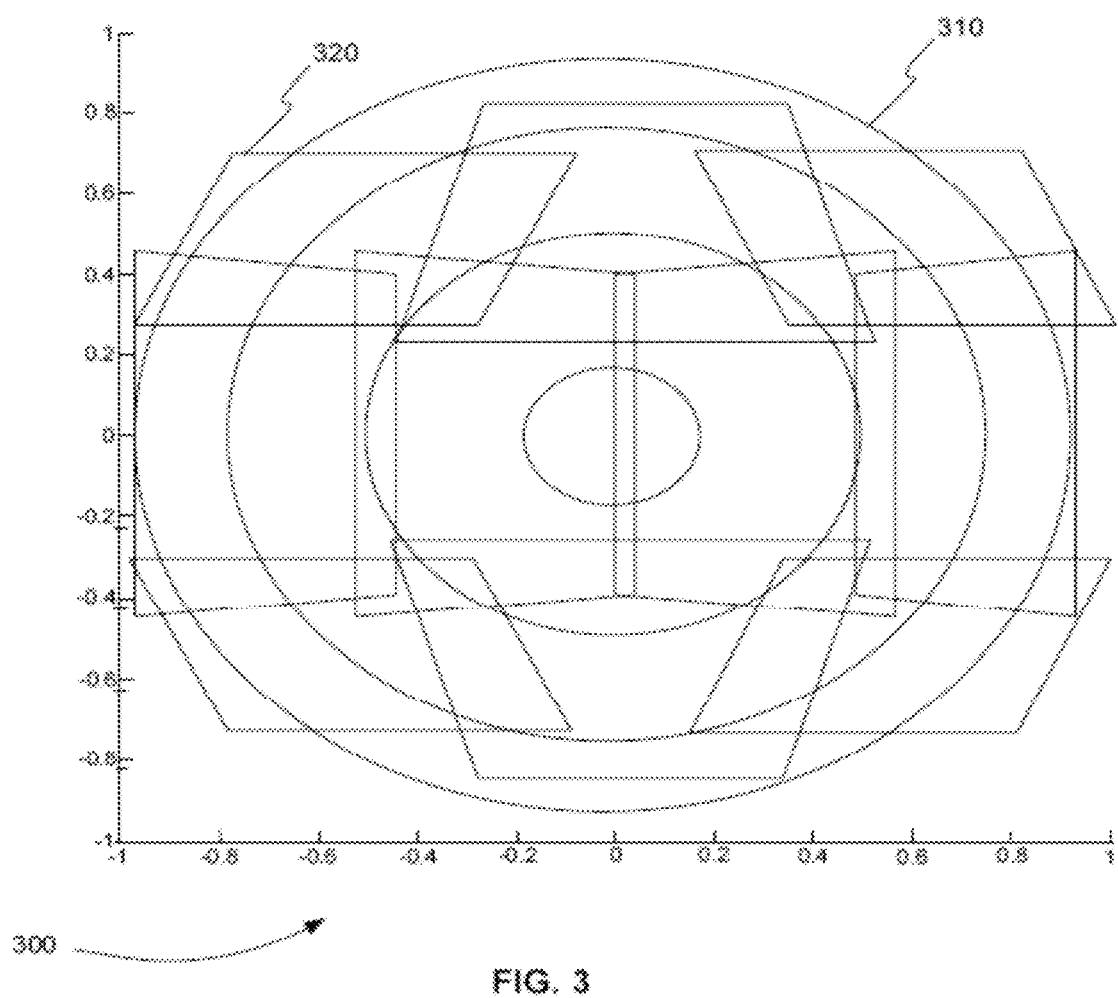
FIG. 3 is an example of a plot of the field of view for the cameras shown in FIG. 2, in accordance with embodiments.

FIG. 3 is an example of a plot 300 of the field of view for each of the cameras 210 shown in FIG. 2, in accordance with various embodiments. Circles 310 represent the location of a user's head. Trapezoids 320 represent the field of view of for each of the one or more cameras 210, shown in FIG. 2, as projected over a sphere concentric with the user's head.

Figure 4:
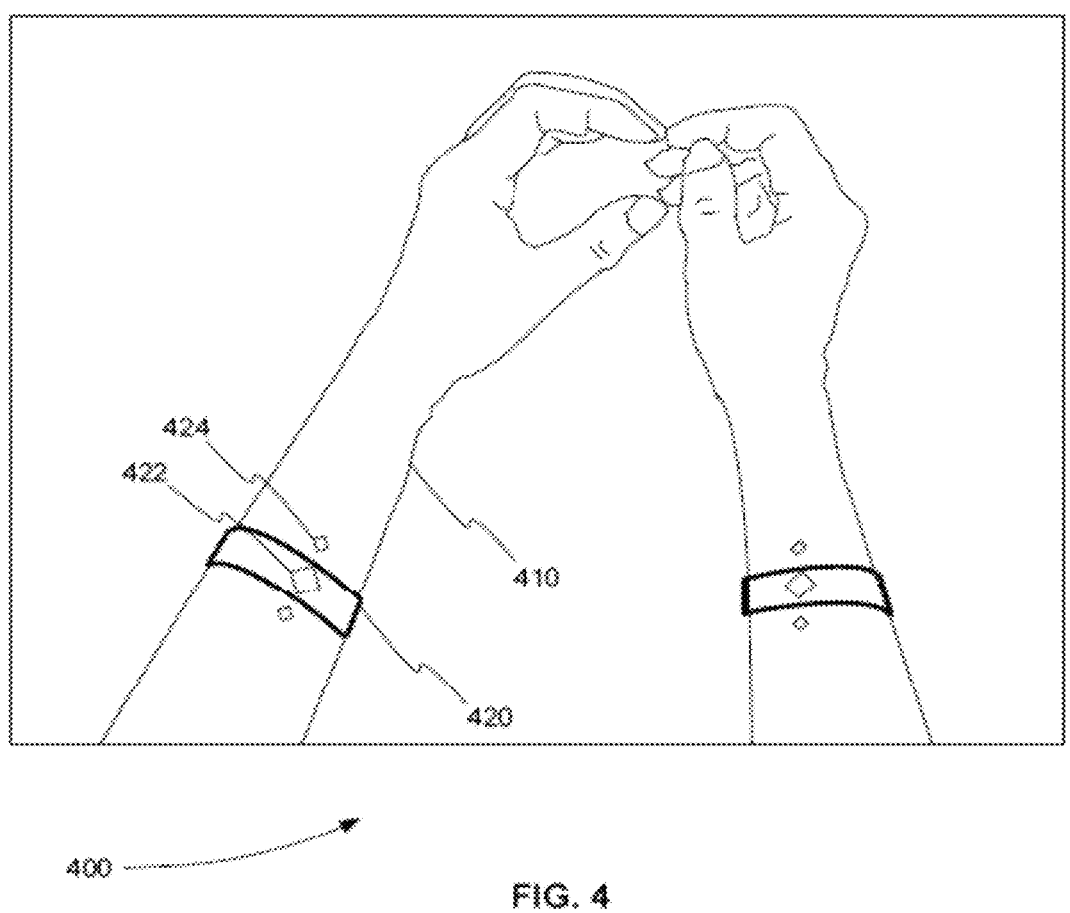
FIG. 4 is an example of a screen shot showing passive markers placed on an object captured by a camera system and tracked, in accordance with embodiments.

FIG. 4 is an example of a screen shot showing passive markers 420 placed on an object 410 being captured by camera system 200 of FIG. 2 and tracked. In FIG. 4, the object to be tracked is a user's arms 410. Passive markers 420, such as rubber bands, can be placed on the user's arms 410. As shown in FIG. 4, center rectangles 422 show the location of the rubber bands 420 as detected by a camera system. Smaller rectangles 424 denote the direction in which the arms 410 are pointing, as detected by the camera. One or more passive markers 420 can be detected in an image. Rectangles 422 and 424 are one potential representation for use with an algorithm to track the passive markers 420, but rectangles 422 and 424 do not necessarily have to appear on the image being displayed to the user via the personal viewing device 220.

Various embodiments can provide different pieces of information about the tracked objects to an application. An example of this information could include magnitude, position, orientation, velocity, and acceleration of each object. The system can also use prediction algorithms to provide this information even when tracked objects are momentarily outside the field of view of the cameras, or are temporarily hidden from view.

FIG. 4 shows two passive markers 420, for example. One or more passive markers 420 can include identifying information to distinguish objects 410. Identifying information can include, but is not limited to, color or pattern and/or some other property. A pattern can include a barcode, for example. Such coding could be used to distinguish between various markers, and the objects to which they are attached. For example, the marks can be used to distinguish between a marker on the left hand and on the right hand of an individual or between the marker on a hand and a marker on a weapon.

In various embodiments, the identifying information can also be used to determine the orientation of objects 410. For example, different parts of a passive marker 420 can have different identifying information; half of passive marker 420 can have one color and the other half can have a different color.

Passive markers 410 can simplify image processing and allow low resolution cameras to be used. Low resolution cameras can record at a high frame per second rate allowing high speed motion to be captured, and thus reduce the overall cost of a system.

Various embodiments can implement real-time target tracking using any number of algorithms. Various embodiments (including augmented-reality goggles and various processors) can request a video or image be analyzed using a real-time tracking algorithm. One embodiment of a real-time target tracking, in accordance with embodiments, can first convert pixels from a standard RGB image (in the sRGB color space) (e.g. from a frame of a video input signal) into L*A*B* color space. This can be accomplished by first converting the sRGB image into the linear RGB color space:

$$C_{linear} = \begin{cases} \dfrac{C_{srgb}}{12.92}, & C_{srgb} \leq 0.04045 \\ \left(\dfrac{C_{srgb}+a}{1+a}\right)^{2.4}, & C_{srgb} > 0.04045 \end{cases}$$

Where a is 0.055 and C is either R, G or B.

Since this transformation is independent for R, G and B, embodiments can use a precalculated 256-element lookup table. The image is then converted from the linear RGB color space to the XYZ color space:

$$\begin{bmatrix} X \\ Y \\ Z \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \begin{bmatrix} R_{linear} \\ G_{linear} \\ B_{linear} \end{bmatrix}$$

Embodiments of this conversion can require three multiply-add operations for each pixel. The image is then converted from the XYZ color space to L*A*B* color space:

$$L^* = 116 f(Y/Y_n) - 16$$
$$a^* = 500[f(X/X_n) - f(Y/Y_n)]$$
$$b^* = 200[f(Y/Y_n) - f(Z/Z_n)]$$

Where:

$$f(t) = \begin{cases} t^{1/3} & \text{if } t > \left(\dfrac{6}{29}\right)^3 \\ \dfrac{1}{3}\left(\dfrac{29}{6}\right)^2 t + \dfrac{4}{29} & \text{otherwise} \end{cases}$$

And where $X_n$, $Y_n$ and $Z_n$ are the CIE XYZ tristimulus values of the reference white point (the subscript n stands for "normalized"). $X_n$=95.047; $Y_n$=100; $Z_n$=108.883. Since $X_n$, $Y_n$ and $Z_n$ are fixed, embodiments can have f(t) be from 0 to 1, and thus $f(X/X_n)-f(Y/Y_n)$ and also $f(Y/Y_n)-f(Z/Z_n)$ can be from −1 to 1. In such embodiments calculations could be made through a lookup table, leaving simple add/multiply operations. Embodiments can have L* values restricted to the range [0,100]. Embodiments can also have A* and B* values be restricted to the range [−100,100]. Embodiments can also use a 16-bit color space for RGB (such as RGB565) which could allow a complete lookup table implementation of the above using a 64K×3 byte look up table.

Embodiments can then perform an L*A*B* threshold analysis on the image that is in the L*A*B* color space. A pixel with L*A*B* coordinates can be deemed of interest if one or more of the following conditions hold:

$$\begin{cases} L_{low} \leq L^* \leq L_{high} \\ A_{low} \leq A^* \leq A_{high} \\ B_{low} \leq B^* \leq B_{high} \end{cases}$$

The low and high thresholds can be specified by the requester of the analysis. Embodiments can provide one or more set of thresholds, one for each target to be tracked. Each set of thresholds can include values for one or more of the parameters L*, A*, B*. Pixels that meet these criteria are deemed to be of interest and/or can be said to be a "1" pixel. Embodiments can also determine a pixel of interest by comparing its color value in another space (e.g., RGB, CMYK, YUV, and/or the like) to a set of thresholds and/or to the value of another coordinate of its color value. For example, a pixel might be deemed of interest if the Red component of its color in the RGB color space is twice as large as the Green component of its color in the RGB color space.

Examples of thresholds sent by the analysis requester can include, for example, if a red band were being tracked the threshold values might be:

$$\left\{\begin{array}{l} \text{Red} > 4*\text{Green} \\ A_{low} \leq A^*; A_{low} = \text{level of } 97^{th} \text{ percentile of } A^* \text{ histogram} \\ B_{low} \leq B^*; B_{low} = \text{level of } 90^{th} \text{ percentile of } B^* \text{ histogram} \end{array}\right\}$$

If a yellow band were being tracked the threshold values might be:

$$\left\{\begin{array}{l} A^* \leq A_{high}; A_{high} = \text{Level of } 80^{th} \text{ percentile of } A^* \text{ histogram} \\ B_{low} \leq B^*; B_{low} = \text{Level of } 97^{th} \text{ percentile of } B^* \text{ histogram} \end{array}\right\}$$

If a green band were being tracked the threshold values might be:

$$\{A^* \leq A_{high}; A_{high} = \text{Level of } 2^{nd} \text{ percentile of } A^* \text{ histogram}\}$$

Figure 5A:
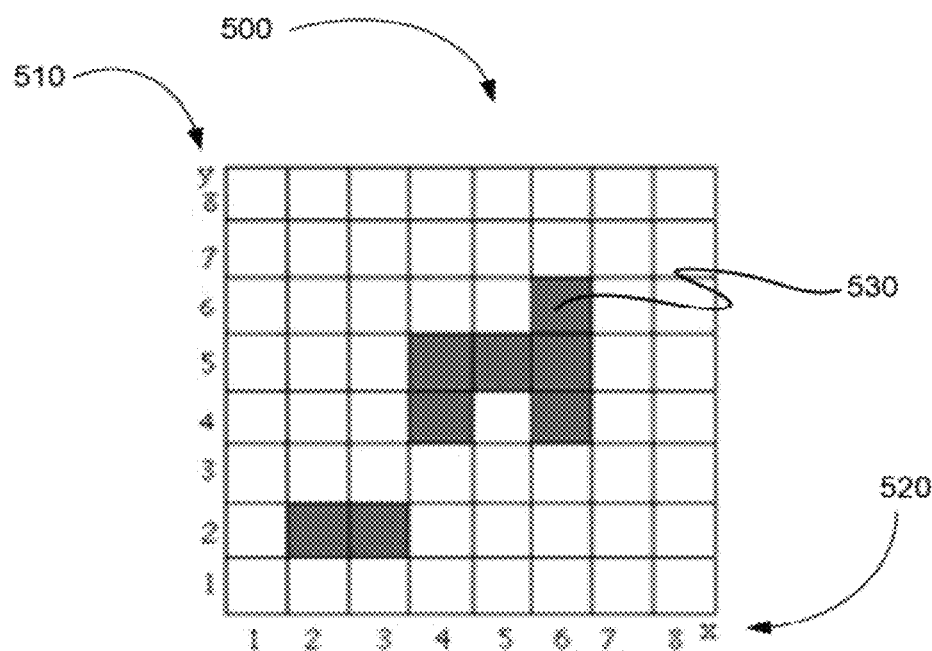
FIG. 5a illustrates an example of an image which is to be run-length encoded in accordance with an embodiment

After the threshold analysis, embodiments can perform run-length encoding (RLE) of target pixels (e.g. the pixels deemed to be of interest as discussed herein, and/or which can be said to be a "1" pixel). Embodiments can report the results of the RLE to the requester of the analysis. In this embodiment binary run-length encoding splits data into runs of zeros and ones, which can compresses the data. FIG. 5a depicts an image 500 that resulted from an exemplary threshold analysis. Though depicted is an 8×8 pixel image, the image can be of any dimension. It has a y-axis 510 and x-axis 520. The image has several "1" pixels 530, that were deemed to be of interest by the analysis. For each row on the y-axis the RLE encodes starting pixel x-coordinate and length of the sequence of "1" pixels. If a row does not have any "1" pixels, it need not be encoded. For example, the coding of the image 500, starting from row 1 and going to row 8, is shown in Table 1:

TABLE 1

| Row | Start pixels | Length |
|---|---|---|
| 2 | 2 | 2 |
| 4 | 4 | 1 |
| 4 | 6 | 1 |
| 5 | 4 | 3 |
| 6 | 6 | 1 |

Various embodiments do not have to store the image. The RLE can be performed sequentially as pixels arrive, and then immediately reported to the requestor. For example, each row that has a "1" pixel could start a new line. If rows 7 and 8 were all "1" pixels, the embodiment would report two entries: one for row 7 (row: 7; start: 1; length: 8) and one for row 8 (row: 8; start: 1; length: 8). Embodiments can also calculate and report the RLE for each target separately. In various embodiments, the RLE data is analyzed by a processor, field-programmable gate array (FPGA), an application specific integrated circuit (ASIC), a digital signal processor (DSP) and/or the like to identify groups of connected "1" pixels (sometimes called "blobs"). In various embodiments, the blobs may be analyzed directly from the "1" pixels; without encoding the "1" pixels as RLE data. In various embodiments, attributes of one or more blobs such as area, size of bounding box, size of long, and short axis, eccentricity, curvature and/or other attributes can be calculated. In various embodiments, such attributes may be used to identify blobs that have a higher likelihood to be the actual objects, being tracked, as opposed to system artifacts. For example, if wrist bands are used as markers, the system may give preference to objects that are elongated as opposed to round. In various embodiments, morphological operators such as dilution, hole closure and the likes may be used to improve the list of "1" pixels before converting them into blobs.

Embodiments can use one or more characteristics of A* and B* elements of the L*A*B* color space to facilitate real-time target tracking. For example, embodiments can use the characteristic that A* and B* components are less sensitive to light changes, and are typically more representative of a particular color type and not necessarily its intensity.

Various embodiments can also calculate the histogram of A* and B* components of the L*A*B* color images. These histograms can be used, for example, to calculate the thresholds used in L*A*B* threshold analysis. Embodiments can restrict the range of values for A* and B* components to [−100,100]. Embodiments can calculate histograms for every frame of video submitted to the embodiment. Embodiments can, if necessary for timing reasons, exclude the last few rows in a frame from one-dimensional histogram calculation so that the histogram calculation can finish shortly after the end of the frame.

Various embodiments can calculate a two-dimensional histogram for both A* and B* components. Embodiments of the histogram can be of size 16×16 (i.e. a total of 256 elements). This can be achieved by normalizing values of the A* and B* components (Embodiments can ignore the L* components). For example, $A_{normalized}$ and $B_{normalized}$ can be calculated using the following formulas:

$$A_{normalized} = \text{round}(A^*/10), \text{ clamped at } [-7 \text{ to } 8]$$

$$B_{normalized} = \text{round}(B^*/10), \text{ clamped at } [-7 \text{ to } 8]$$

Once $A_{normalized}$ and $B_{normalized}$ are determined for each pixel, 1 can be added to the count of the pixels with this $A_{normalized}$ and $B_{normalized}$ values. These values can be reset to 0 after a number of frames. Embodiments can store the histogram in a 256 entry RAM array, each with 24 or 32 bit entries. In various embodiments, such histograms can be used to calibrate the scene in which the personal viewing device operates and improve its performance. For example, at the beginning of the operation, the user might be asked to present her hands to the camera and then lower them. Such histograms can help identify the specific colors present on the hand and thus help track the user's hands. In another embodiment, the system can use such histograms to suggest colors of markers, if color markers are being used. For example, if the histogram determines that the space in which the system is operating has large amounts of red objects, it might suggest a color other than red for the markers.

Figure 5B:
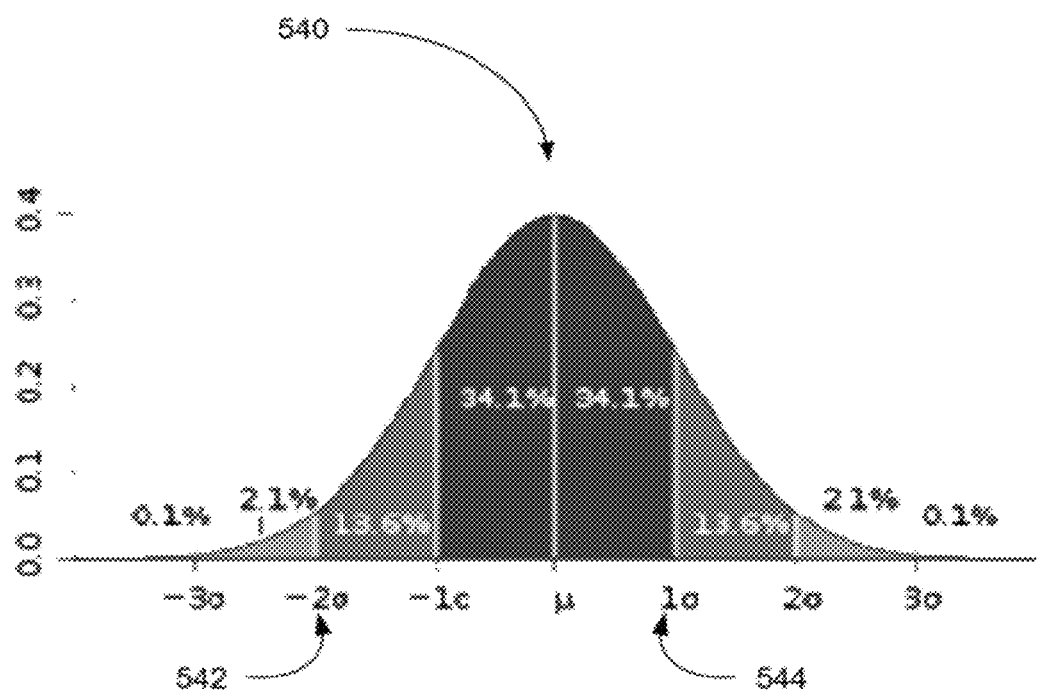
FIG. 5b illustrates an example of a one-dimensional histogram of A* in accordance with an embodiment.

Various embodiments can calculate a one-dimensional histogram of the A* component. The histogram can comprise a total of 201 elements. One method for calculating such a histogram is to add 1, for each pixel, to the count of the pixels with this A* value. At the end of the frame, lower and upper percentiles are calculated. A lower percentile P is the value of A such that the sum of all histogram bins up to this value equals P percent of the total pixels. An upper percentile P is the value of A such that the sum of all histogram bins up to this value equals P percent of the total pixels. For example, FIG. 5b depicts an exemplary histogram 540. Reference numeral 542 points where −20 is the lower 2.4 percentile. Reference numeral 544 points to where 10 is the upper 84.2% percentile (i.e. 100%-0.1%-2.1%-13.6%).

Embodiments can also calculate a one-dimensional histogram of the B* component. One method for calculating such a histogram is to add 1, for each pixel, to the count of the pixels with this B* value. At the end of the frame, lower and upper percentiles are calculated. A lower percentile P is the value of B such that the sum of all histogram bins up to this value equals P percent of the total pixels. An upper percentile P is the value of B such that the sum of all histogram bins up to this value equals P percent of the total pixels.

One problem with tracking hands, from the perspective of a user (i.e., using one or more outward pointing cameras), is being able to distinguish the hands from the surrounding background. Various embodiments can overcome this problem. Some embodiments can increase the aperture of one or more of the cameras on the HMD. By increasing the aperture and setting the focal length correctly, these embodiments can set the depth of field to match the approximate distance of the hands from the head of a user. Subsequently, the images captured by the adjusted cameras will show the hands and other near objects in focus, while farther objects and the background will be out of focus. Image processing algorithms can detect which objects are in focus and which are not in focus, thus increasing the accuracy of hand detection.

Some embodiments can implement real-time target tracking of, for example, hands using color values that correspond to skin tones, which can facilitate the tracking of body parts (including hands and/or fingers) without markers.

FIG. 5*c* depicts an embodiment 570 of how a real-time target tracking algorithm might format some of the data output to a requestor. Though the algorithm, as depicted, is implemented in a field-programmable gate array (FPGA), embodiments are not meant to be limited to such. FIGS. 5*d* and 5*e* depict an embodiment 580 of a subset of commands that a requestor could send to an embodiment of a real-time tracking algorithm system.

Various embodiments can also use the information received/deduced from one or more of the cameras and/or sensors to determine the position of the item to be tracked. An example of an embodiment 1100 of one such method is depicted in FIG. 11. Depicted is an embodiment of a personal viewing device 1110 having multiple cameras 1140. Embodiment 1110 can use knowledge of the specific location and/or orientation of each camera 1140 and/or sensor (not depicted), located thereon, to triangulate the position (e.g., distance and/or direction from an embodiment) of the item 1150 when seen by two or more cameras 1140 and/or sensors, using methods known in the art. Various embodiments can calculate and/or display triangulation tracking lines 1162 to, for example, show the relative position of object 1150. In some embodiments, recent information about the size of a target can be used to calculate its location in case the target is observed by a single sensor. For example, an embodiment can assume that as the target moves closer/farther from the sensor, the detected area would increase/decrease in proportion to the $r^2$ where r is the distance from the target to the sensor.

Various embodiments can also use predictive tracking, Kalman filtering and/or other signal processing algorithms to take into account position and/or orientation information from previous measurements to estimate the likely future position and/or orientation of a target. Embodiments can use such prediction, for example, in the case the target is temporarily obscured.

Figure 6:
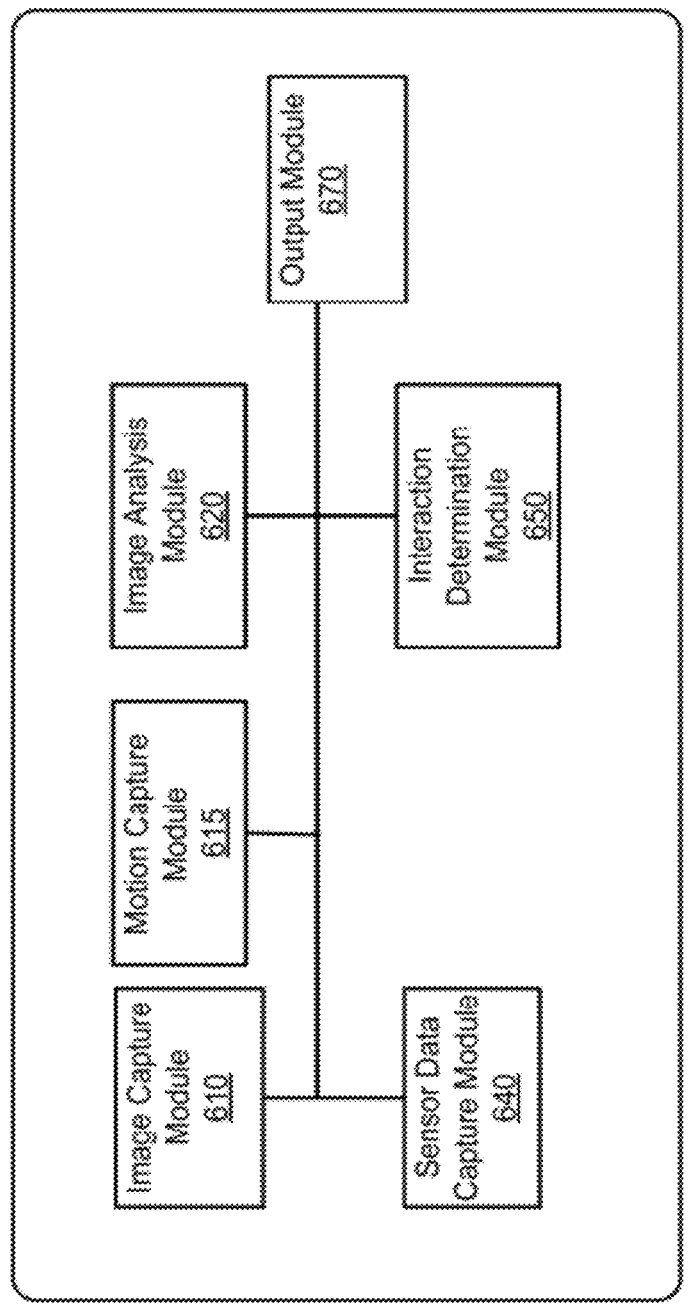
FIG. 6 is a schematic diagram of a processing device/system in accordance with embodiments.

FIG. 6 is a schematic illustration of a processing device/system 600 for interaction analysis, in accordance with some embodiments. In various embodiments the system can be implemented as a device; in various other embodiments it can be implemented as a system. In either case the device/system 600 can be configured to analyze the image and sensor data obtained from the cameras/sensors associated with a personal viewing device. In various embodiments the device/system 600 can be used to implement any number of real-time target tracking algorithms, for example, such as the one discussed with regard to FIG. 5. The device/system 600 can be used to identify objects found within the images and can determine if the objects can be interacted with (either by a user or with one another). The device/system 600 can determine what types of interaction are possible with one or more of the objects and if an interaction is occurring between two or more objects. If an interaction is occurring, the type of interaction that is occurring, e.g., a beverage bottle is being thrown in the trash, instead of being consumed, can be identified.

In various embodiments the processing device/system 600 for interaction analysis can be implemented inside a personal viewing device or, if external, be in communication with a personal viewing device. In various embodiments, the processing device/system 600 can be structurally and functionally similar to the processing device 1004 shown and described with respect to FIG. 10. The personal viewing device that employs the processing device/system 600 can be structurally and functionally similar to the embodiment shown and described with respect to FIG. 2. The processing device/system 600 can be configured to convert captured video data describing an object's real-world positions and movements into positions and movements that fit within predetermined constraints of the virtual world in which a virtual object (e.g., avatar, cursor, representation of an object) can be rendered. Particularly, the processing device/system 600 can employ a set of hardware/software modules to accurately map real-world actor positions and movements to a virtual object rendered within a virtual environment, as described in detail herein. In some embodiments, the processing device/system 600 can employ a set of hardware/software modules to accurately map real-world actor positions and movements to an augmented reality environment as described.

In various embodiments, the processing device/system 600 can be implemented as a processing system, where the individual modules can be implemented in separate locations and where each module is in communication with each other. For example, the image capture module 610 and sensor data module 640 can be implemented in a personal viewing device. The other modules could be implemented in physically different systems located at different locations. One or more of the modules can be in communication with each other via hard wire, Ethernet, Wi-Fi, Bluetooth, cellular networks, 3G, 4G, LTE or other forms of communications or combinations thereof.

As shown in FIG. 6, the processing device/system 600 for interaction analysis can include an image capture module 610, a motion capture module 615, an image analysis module 620, sensor data capture module 640, interaction determination module 650 and output module 670. Each of those modules can include one or more software (stored and executed in hardware) and/or hardware-based modules or components. In some embodiments, the processing device/system 600 can include a processor, a CPU, or the like, which is configured to execute the modules 610-670. In some embodiments, each of the modules 610-670 in the processing device/system can include a field-programmable gate array (FPGA), an application specific integrated circuit (ASIC), a digital signal processor (DSP) and/or the like. Though the depicted embodiment shows only one instance of each module 610-670, various embodiments can be implemented using one or more instances of one or more of the modules 610-670, all of which can be used to perform interaction analysis.

In various embodiments, the image capture module 610 can be configured to receive data associated with images captured from outward facing cameras 210. These images can be directly from cameras 210, or indirectly, after undergoing some form of processing.

In various embodiments, the motion capture module 615 can be configured to receive data associated with image and sensor data obtained from the cameras/sensors associated with a personal viewing device. Embodiments can analyze this data to determine information regarding various objects captures by the system (e.g., the direction and velocity).

In various embodiments, the sensor data capture module 640 can be configured to receive data associated with sensors 270. The data can be received directly from sensors 270, or indirectly, after undergoing some form of processing.

In various embodiments, the image analysis module 620 can be configured to process the information from image capture module 610, motion capture module 615, and, sensor data capture module 640. In various embodiments the image analysis module 620 can identify objects (including body parts) depicted within the images, whether or not they have a marker attached. The image analysis module 620 can determine if the objects can be interacted on (e.g., is an interactive object), either by a user or with each other. The image analysis module 650 can also coordinate a display of images based on the data received by the image capture module 610, the motion capture module 615, sensor data capture module, or combinations thereof. The image analysis module 620 can also determine what types of interactions are possible amongst the user and/or the objects. For example, in various embodiments the image analysis module 620 can employ one or more computer vision algorithms (e.g., algorithms used to identify objects within an image like a user's hands or a bottle, real-time target tracking algorithms and/or the like). It could also use other information like barcode data taken from a bar code reader sensor or the image itself. The image analysis module 620 can access additional information, e.g., one or more databases to identify objects found within the images and the types of interaction that are possible. These databases can include Universal Product Code databases, International Standard Book Number Databases, image databases and other databases. In various embodiments, the image analysis module can perform analysis in multiple stages. For example, the image analysis module can detect the location of a wrist band marker, and then use the known location of the wrist to estimate where the palm of the hand is. In various embodiments, this estimate can be used to then identify the location of individual fingers.

The interaction determination module 650 can be configured to receive data from the image capture module 610, the image analysis module 620, the sensor data capture module 640 or combinations thereof. In some embodiments, the interaction determination module 650 is a combination of the image capture module 610, the motion capture module 615, the image analysis module 620 and the sensor data capture module 640. The interaction determination module 650 can determine whether the objects found within the image are interacting, how they are interacting, whether this is a new interaction or the continuation of a previous interaction. The interaction determination module 650 can also determine parameters that are associated with the interaction, i.e., which objects are involved, direction of motion, velocity, location, force applied, amount, and the like. For example, in reference to the earlier example, did the user actually throw a ball or did he drop it instead, what was the velocity of the ball, where was it thrown; did the user drink the entire beverage, or a portion of it, what amount of the beverage was consumed, etc. Various embodiments can display this information to the user in some for, e.g., the direction of motion of an object could be indicated by an arrow emanating from the object. Various embodiments can be used as a gesture engine to analyze gestures. The output module 670 takes determinations made from the interaction module 650 and outputs it to the system. The system then decides how to respond and what to present to the user.

Figure 7A:
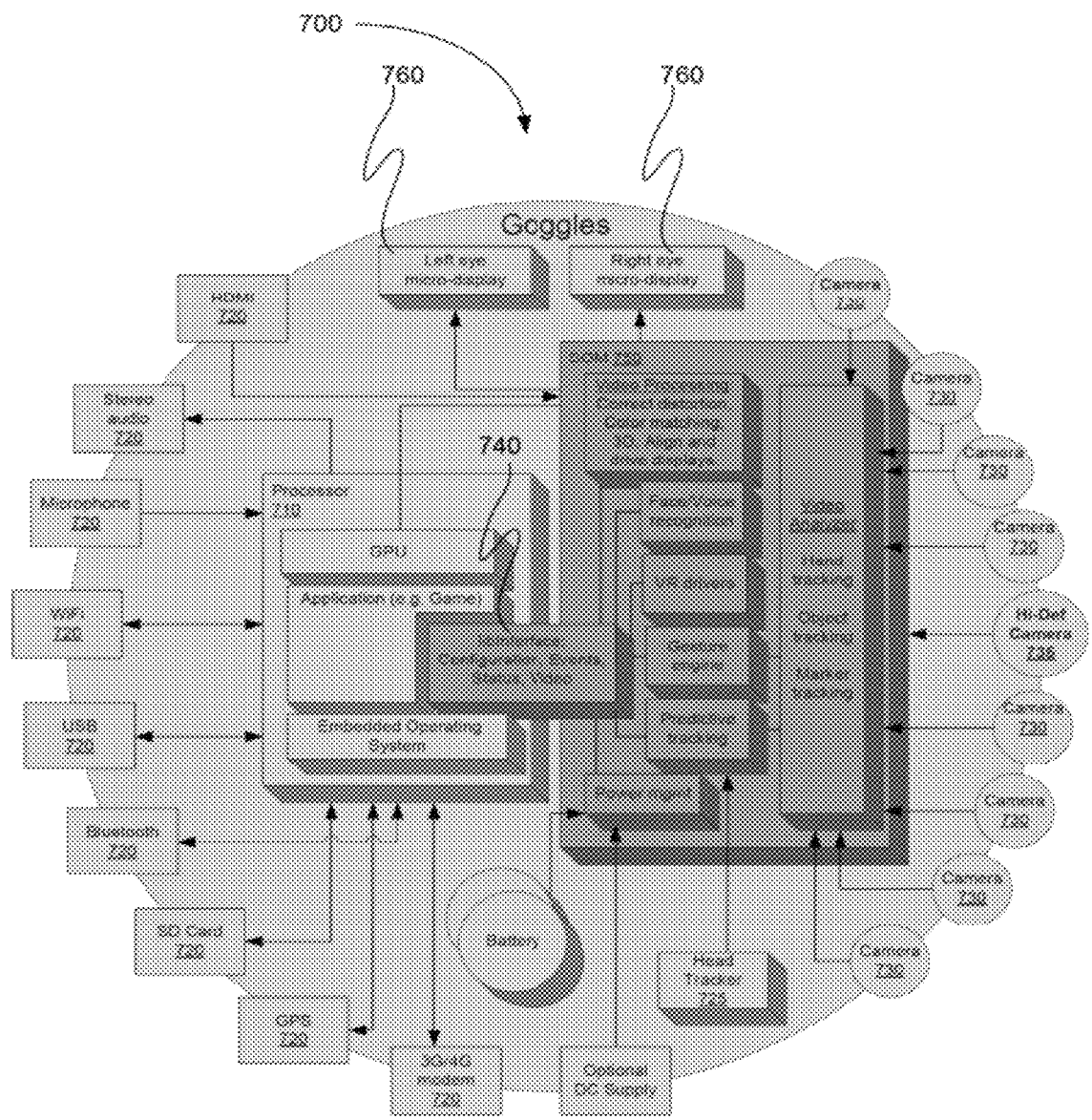
FIG. 7a illustrates a system in accordance with embodiments.

FIG. 7a depicts a personal viewing system in accordance with embodiments. It should be noted that though FIG. 7 depicts a system 700, embodiments may be implemented as one or more individual devices and/or components that are in communication with each other. A processor 710 in communication with input and/or output devices (I/O devices) 720. The processor 710 is in communication with System On Module (SOM) 750 though library interface 740. SOM 750 includes a Video Processing unit, Face/Voice recognition unit, Virtual Reality (VR) driver unit, Gesture Engine unit, Predictive tracking unit, and/or a Video Analyzing Unit and/or a power management unit. The SOM 750 is in communication with left and right eye micro-displays 760, a Battery, an optional direct current (DC) power supply, cameras 730, and/or optional High-Definition camera 735 (though only one High-Definition camera is depicted, various embodiments can have one or more such cameras). One or more of the cameras 730, 735 may be outward-facing. The I/O devices 720 can include, however are not limited to, one or more video connectors (e.g., a High-Definition Multimedia Interface (HDMI) connector, DVI connector, VGA connector, display port connector, and/or the like) stereo audio output, microphone, WiFi interface, USB interface, Bluetooth interface, SD Card socket, and/or a 3G/4G modem. I/O devices 720 can also include sensors such as a GPS sensor, head tracking sensor 725 and temperature sensors (not pictured) and/or the like. Embodiments can be powered using a variety of energy sources e.g., solar panels, batteries, fuel cells, and/or the like.

Figure 7B:
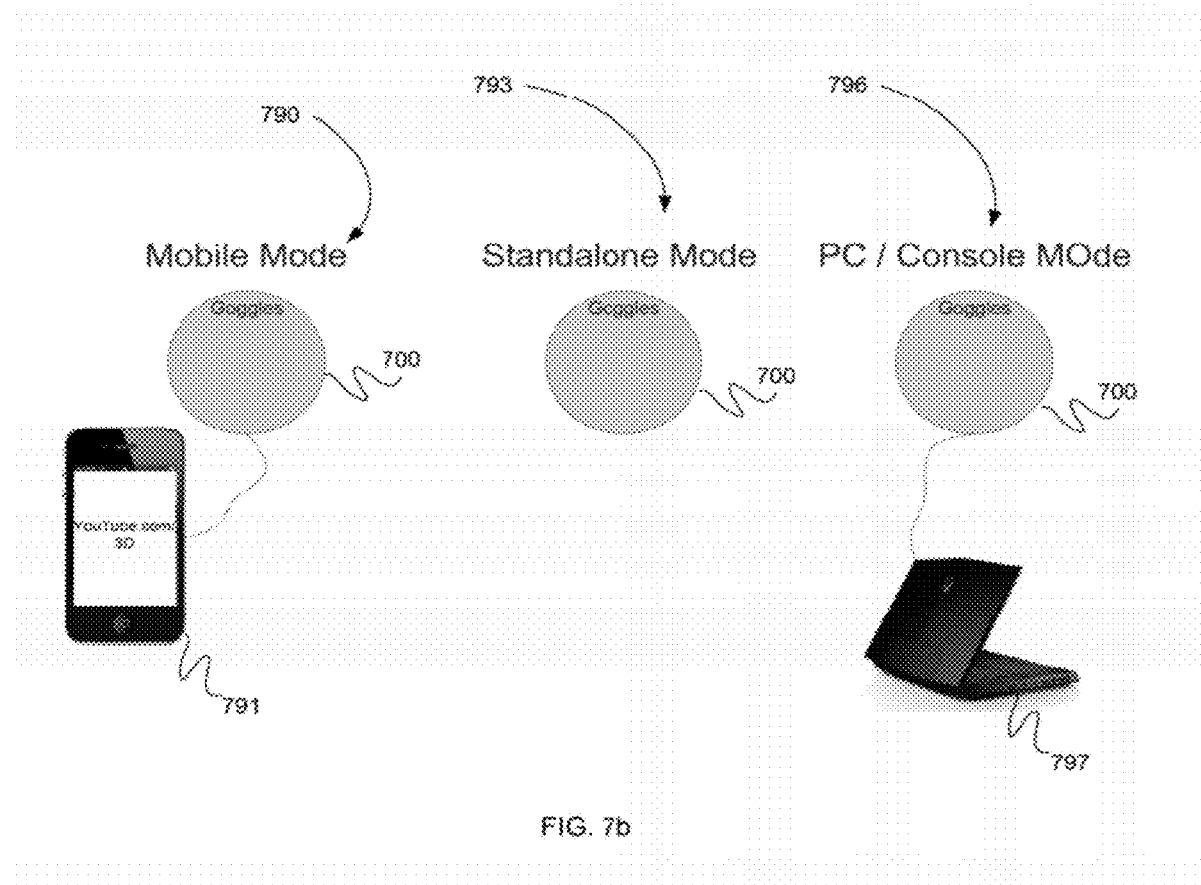
FIG. 7b illustrates operating modes in accordance with embodiments.

FIG. 7b depicts embodiments, for example system 700, operating in one of three modes 790, 793 and 796. Embodiments can also operate in multiple modes simultaneously. In Mobile Mode 790, for example system 700, is in communication with one or more mobile devices 791. Similarly, in PC/Console Mode 796, for example system 700, is in communication with one or more external computing devices 797. In such modes the embodiment can be an interface to the mobile device 791 and/or external computing device 797, accessing and interfacing with some or all the functionality of mobile device 791 and/or external computing device 797. During such operation, for example, system 700 can present the user with visual information through displays 760. The visual information can, for example, include images and/or video that would normally be displayed on the screen of mobile device 791, specialized images and/or video for exclusive display through system 700, or combinations thereof. System 700 can send input to mobile device 791 and/or external computing device 797; such input can result from, for example, the motion of a user's head, I/O devices 720, real-time target tracking (e.g.

marker, object, a user's hand and/or fingers), using one or more camera's 730,735, and/or the like. Such input can also be additionally processed by system 700 before being sent to mobile device 700. In Standalone Mode 793 the system 700 and operate as a standalone mobile device and/or computing device.

In various embodiments, processing can take place at different locations. For example, in some embodiments, e.g., similar to Standalone Mode 793, the algorithmic processing as well as the processing related to the application (such as a game) can execute in the personal viewing device or on a remote computer in communication with the personal viewing device. In other embodiments, e.g., as PC/Console mode 796, a greater share of the application executes on the PC or Console and the personal viewing device can be mainly used as a display and/or a sensor.

For example, a person could use a particular mode to read an electronic book. The user could bring their hand into view of one of the outward facing cameras and gesture as if to turn a page in the book. If in Standalone Mode 793, the electronic book reading application is running, for example, on the apparatus itself. The interaction analysis system of the device recognizes the gesture and causes the application to display the next page. If the device is in Mobile Mode 790 or PC/Console Mode 790, the electronic book reading application could be running on a remote device (e.g. a mobile device and/or computer). The remote device tells the apparatus what to display to the user. When the user gestures to turn the page, the apparatus will again recognize this action. In some embodiments, an apparatus can be configured to notify the remotely running application what type of interaction has occurred. The application can then decide how to react to this information. Other embodiments can be configured to additionally process the interaction. For example, in some embodiments, the processor can interpret the gesture as the user wanting to turn the page of the book and then send a turn page command to the externally running application.

Figure 8A:
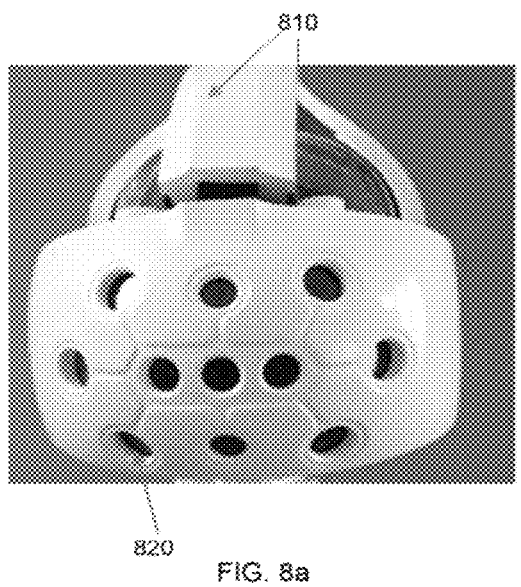
FIGS. 8a-8c illustrate a personal viewing apparatus in accordance with embodiments.
Figure 8B:
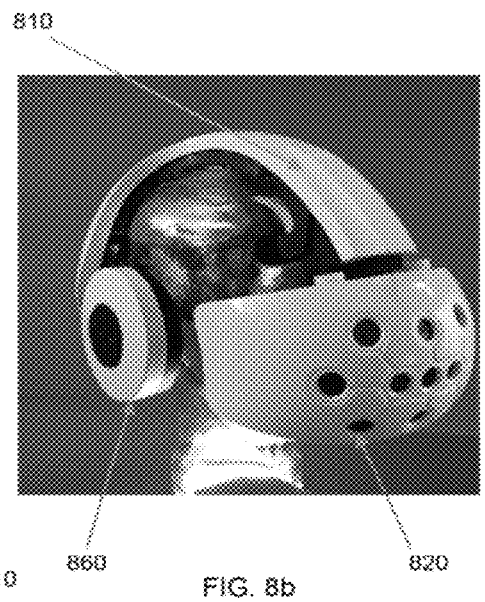
Figure 8C:
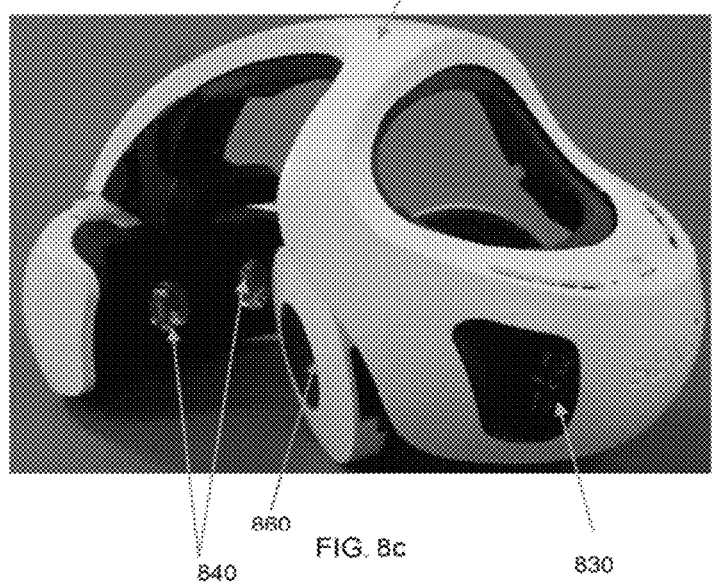
Figure 9A:
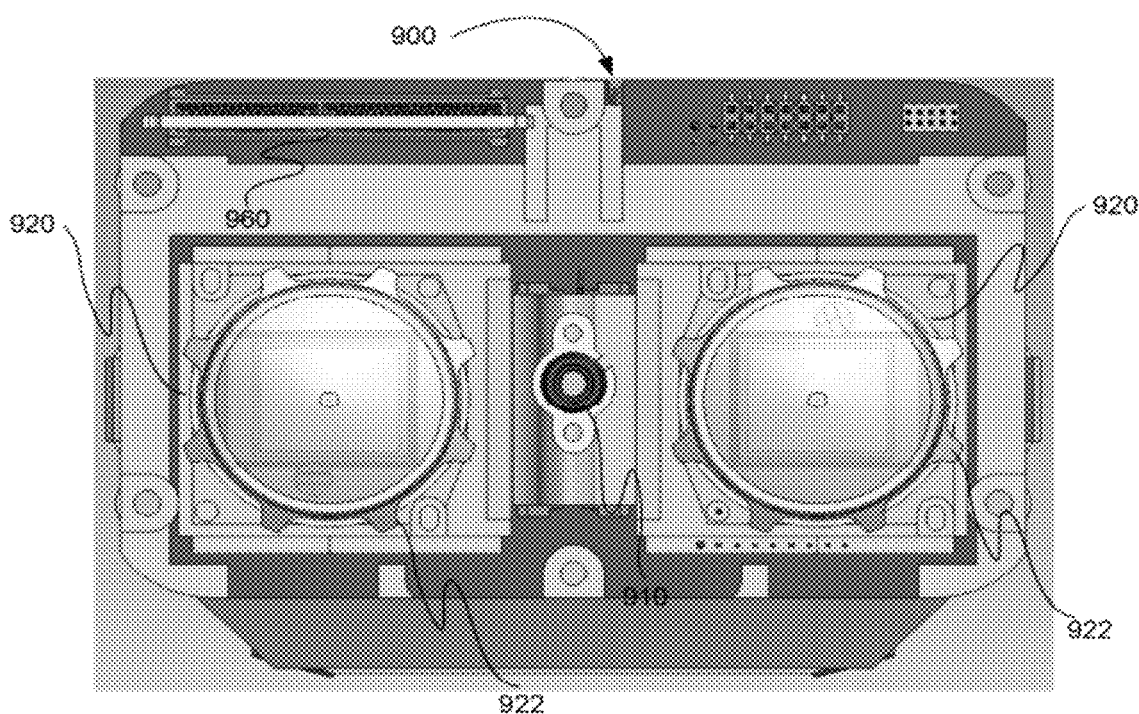
FIGS. 9a-9d are schematic diagrams of a component assembly in accordance with embodiments.
Figure 9B:
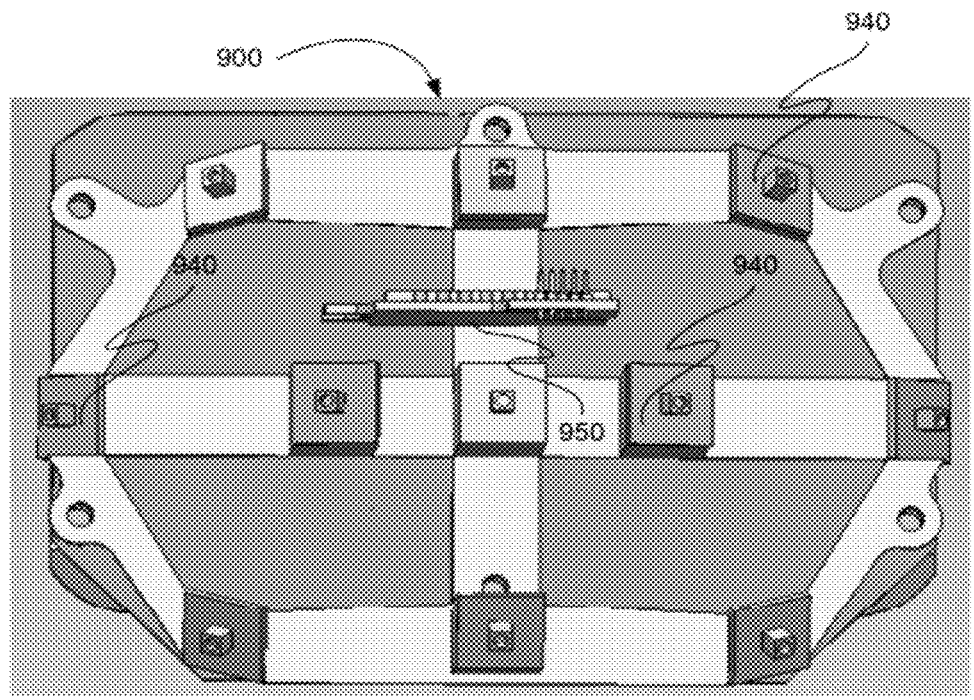
Figure 9C:
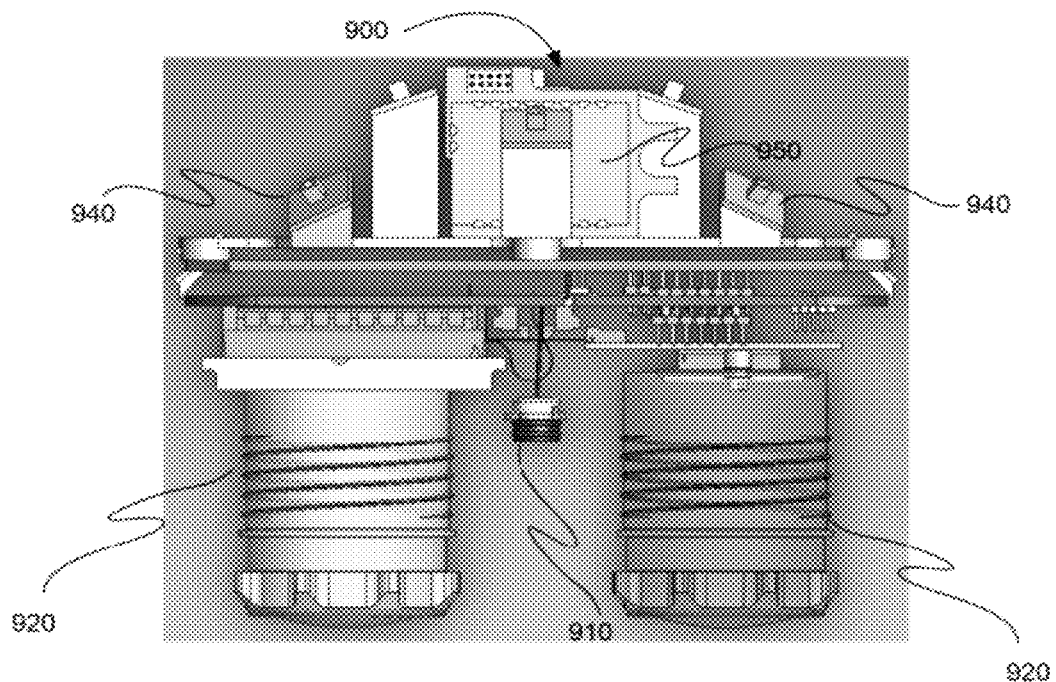
Figure 9D:
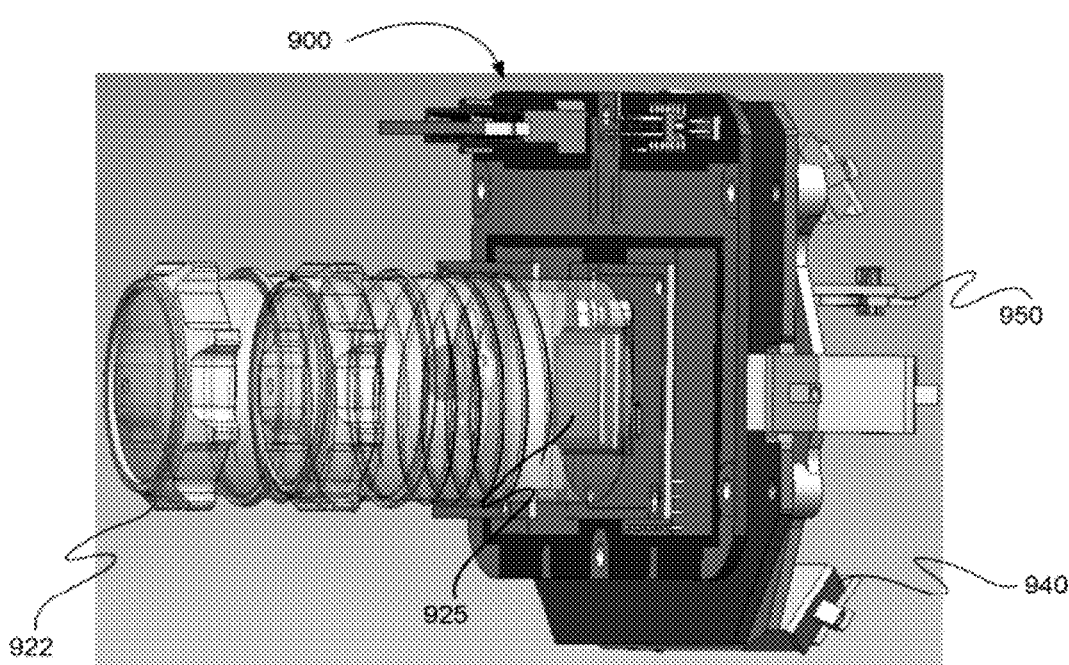

FIGS. 8a-8c depict various views of an embodiment. It includes a personal viewing device 810 configured to be worn by a user. External cameras 820 are coupled to the personal viewing device 810 and face outwardly with respect to the personal viewing device 810. Interface I/O ports 830 can connect the personal viewing device 810 to external devices (e.g., mobile devices, computing devices, input devices, output devices and/or the like) Left and right viewers 840 display images and/or video to the user. Speakers 860 deliver aural information to the user. At least one sensor (not depicted) (e.g., a head tilt sensor, GPS sensor, temperature sensor and/or the like) and at least one processor (not depicted) are located inside the personal viewing device 810. The at least one processor can be in communication with the external cameras 820, I/O ports 830, viewers 840, speakers 860 and the at least one sensor. The processor can also be configured for interaction analysis, among other functions.

FIGS. 9a-9d are a schematic diagram of an embodiment. Component 900 can be integrated in to various embodiments of a personal viewing device. Microphone 910 is an I/O device that can allow a user to interact aurally with the system, e.g., using voice recognition algorithms. Left/right viewer assembly 920 can left/right magnifier's 922, which can magnify the imager/video displayed to the user on left/right displays 925 (e.g., LCD, OLED, LCOS, pico projector and/or the like). Camera boards 940 can be used to couple one or more outward-facing cameras to the personal viewing device. Head tracker assembly 950 can contain one or more accelerometers that can measure the acceleration and tilt of a user's head in any direction. Connector 960 can be used to connect the component 900 to one or more processors of the personal viewing device.

Figure 10:
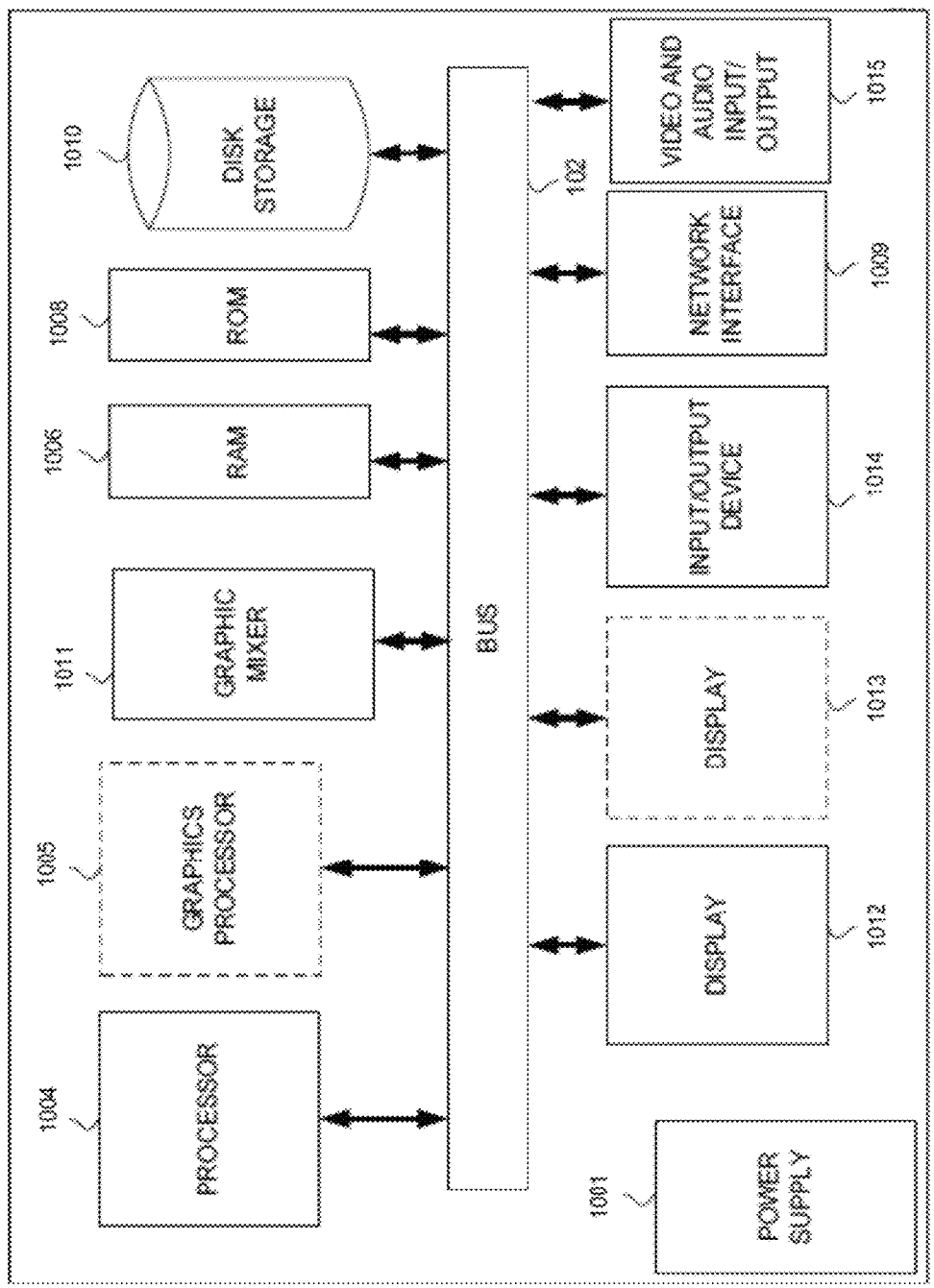
FIG. 10 is a block diagram that illustrates a processing system, in accordance with various embodiments.

With regard to FIG. 10, the processing system 1000 can be implemented on an electronic board or board set. The processing system 1000 can also be implemented and integrated into a chip or chipset as is sometimes called "System on a Chip".

Processing system 1000 includes a Power Supply 1001 or another energy source for distributing and regulating power to the various components. The source of such power can be from any source e.g., an electrical outlet or a battery or a solar panel or a mechanism that translates user motions into power. The Power Supply 1001 converts and regulates the power to meet power needs desired by the various components. Processing system 1000 also includes a bus 1002 or other communication mechanism for communicating information such as data or video between the various components, and a processor 1004 coupled with bus 1002 for processing information. Processing system 1000 can also include a graphics processor 1005 that assists processor 1004 with generating graphics, text, or images as well as performing various image transformations. For instance, the graphics processor can perform geometrical transformations of an image to compensate for any optical distortion caused by the viewing system of the personal display device. Processing system 1000 also includes a memory 1006, which can be a random access memory (RAM) or other dynamic storage device, coupled to bus 1002 for determining base calls, and instructions to be executed by processor 1004 and by graphics processor 1005. Memory 1006 also may be used for storing temporary variables, images or other intermediate information during execution of instructions to be executed by processor 1004 and by graphics processor 1005. Processing system 1000 further includes a read only memory (ROM) 1008 or other static storage device coupled to bus 1002 for storing static information, videos, graphics, sounds, and instructions for processor 1004 and graphics processor 1005. A storage device 1010, such as a magnetic disk or optical disk, is provided and coupled to bus 1002 for storing information, videos, graphics, sounds and instructions.

Processing system 1000 may be coupled via bus 1002 to a display 1012, such as a liquid crystal display (LCD), an organic light emitting diode display (OLED), or a miniature projector ("pico projector") of a personal viewing device, for displaying information to a user. Processing system 1000 might include additional displays such as display 1013 which might be used to provide different images to each eye to provide a stereoscopic 3D effect. Display 1013 might also be used in combination with Display 1012 to provide a higher-resolution image to the eye. An input/output device 1014, is coupled to bus 1002 for communicating information and command selections to and from processor 1004 and graphics processor 1005. Input/output device 1014 can include, but is not limited to, a camera or a set of cameras, an eye tracker, a head tracker, a position tracker, a headphone set, a microphone, a global positioning satellite (GPS) device, a motion sensor, a glove, a communications device, a pointing device, a proximity sensor, biometric sensors (e.g. heart rate, conductance, EEG), an external memory, various indicators, an accelerometer, or a selection device. Processing system 1000 may also include network interface 1009 that can connect computer system 1000 with other computes, networks, the Internet, storage devices via communications links such as Wi-Fi, Bluetooth, cellular networks such as 3G or 4G, wired connections and more.

Consistent with various embodiments, results are provided by processing system 1000 in response to processor 1004 and graphics processor 1005 executing one or more sequences of one or more instructions contained in memory 1006 or read only memory 1008. Such instructions may be read into memory 1006 from another computer-readable medium, such as storage device 1010 or read only memory 1008. Execution of the sequences of instructions contained in memory 1006 causes processor 1004 and graphics processor 1005 to perform the process described herein. Alternatively hard-wired circuitry may be used in place of or in combination with software instructions to implement the present teachings. Thus implementations of the present teachings are not limited to any specific combination of hardware circuitry and software.

The processing system 1000 may include a video and audio input/output 1015 that allows processing system 1000 to accept external video or audio sources such as from cameras. Video and audio input/output 1015 also allows processing system 1000 to generate video or audio sources for outside use, such as to present on an external monitor or to project on a wall or other reflective surface using a pico-projector and to be experienced with headphones or to be transmitted over a wireless network. The processing system 1000 may include a Graphic Mixer 1011 that could combine or overlay one more images, videos or graphics with another. For instance, it could combine video signal coming from a camera connected to input/output device 1014 with graphics generated by processor 1004 or graphics processor 1005. Graphics mixer 1011 could also scale, move or otherwise transform an image, video or graphic prior to such combination. For instance, it could create a "picture in picture" showing a reduced version of video coming from a camera on top of the graphics generated by processor 1004 or graphics processor 1005. For instance, it could create an "augmented reality" by showing annotating symbols over a live camera image.

The term "computer-readable medium" as used herein refers to any media that participates in providing instructions to processor 1004 and graphics processor 1005 for execution. Such a medium may take many forms, including but not limited to, non-volatile media, volatile media, and transmission media. Non-volatile media includes, for example, optical or magnetic disks, such as storage device 1010. Volatile media includes dynamic memory, such as memory 1006. Transmission media includes coaxial cables, copper wire, and fiber optics, including the wires that comprise bus 1002.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a memory card, a memory stick, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 1004 and graphics processor 1005 for execution. For example, the instructions may initially be carried on the magnetic disk of a remote computer. The remote computer can load the instructions into its dynamic memory and send the instructions over a telephone line using a modem. A modem local to processing system 1000 can receive the data on the telephone line and use an infra-red transmitter to convert the data to an infra-red signal. An infra-red detector coupled to bus 1002 can receive the data carried in the infra-red signal and place the data on bus 1002. Bus 1002 carries the data to memory 1006, from which processor 1004 and graphics processor 1005 retrieves and executes the instructions. The instructions received by memory 1006 may optionally be stored on storage device 1010 or memory 1006 either before or after execution by processor 1004.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In various embodiments, motion tracking information from multiple cameras is used in a variety of applications. These applications can include, but are not limited to, robotics, simulation, three-dimensional modeling, medicine, navigation assistance, personalized display of information and gaming. Embodiments can provide for natural interaction of a human with a software application or a machine.

It is to be understood that embodiments may be implemented in various forms of hardware, software, firmware, special purpose processors, or a combination thereof. One embodiment may be implemented in software as an application program tangibly embodied on a program storage device. The application program may be uploaded to, and executed by, a machine comprising any suitable architecture.

It should also be understood that the above description is only representative of illustrative embodiments. For the convenience of the reader, the above description has focused on a representative sample of possible embodiments, that are illustrative of the principles of various embodiments, and has not attempted to exhaustively enumerate all possible variations. That alternative embodiments may not have been presented for a specific portion of the invention is not to be considered a disclaimer of those alternate embodiments. Other applications and embodiments can be straightforwardly implemented without departing from the spirit and scope of the invention. It is therefore intended, that the invention not be limited to the specifically described embodiments, but the invention is to be defined in accordance with that claims that follow. It can be appreciated that many of those undescribed embodiments are within the literal scope of the following claims, and that others are equivalent.

What is claimed is:

1. An apparatus, comprising:
   a personal viewing device configured to display an image of a simulated environment, the personal viewing device configured to be worn by a user;
   at least one sensor coupled to the personal viewing device;
   at least one camera coupled to the personal viewing device and facing outwardly with respect to the personal viewing device; and
   a processor in communication with the personal viewing device, the at least one sensor and the at least one camera, the processor configured to:
   create the simulated environment, the simulated environment including the user,
   define a representation of the user's health within the simulated environment,
   identify a projectile captured by the camera and assign a health modifier to the projectile,
   identify the projectile striking the user, and
   modify the representation of the user's health within the simulated environment based on the projectile striking the user.

2. The apparatus of claim 1, wherein the processor is configured to identify that the projectile struck the user based on data received by the at least one camera.

3. The apparatus of claim 1, wherein the at least one sensor is at least one of a position sensor, a motion sensor, a thermal sensor, a moisture sensor, a pressure sensor, a light sensor or an audio sensor.

4. The apparatus of claim 1, wherein the processor is configured to identify an object as the projectile and identify a type of physical interaction that is possible with the projectile.

5. The apparatus of claim 1, wherein the processor is configured to cause the personal viewing device to display a representation of the projectile in the image based on data received from the at least one camera, the representation of the projectile being different from an image of the projectile.

6. The apparatus of claim 1, wherein the processor is configured to identify a type of physical interaction from a plurality of types of physical interactions associated with the projectile in the image.

7. The apparatus of claim 1, wherein the camera is one of a plurality of cameras, the plurality of cameras being configured for motion capture.

8. The apparatus of claim 1, wherein the processor is configured to calculate a distance to the projectile in the image.

9. The apparatus of claim 1, wherein the processor is configured to calculate a direction to the projectile in the image.

10. A non-transitory processor-readable medium storing code representing instructions to be executed by a processor, the code comprising code to cause the processor to:
    receive data from an outward-facing camera coupled to a personal viewing device, the personal viewing device configured to be coupled to a user;
    receive data from a sensor coupled to the personal viewing device;
    define a simulated environment based, in part, based on the data received from the outward-facing camera and the sensor, the simulated environment including the user, the user having a representation of health within the simulated environment, the simulated environment including a representation of a projectile captured by the camera;
    display a plurality of images of the simulated environment;
    determine that the projectile captured by the camera can be physically interacted with;
    assign a health modifier to the projectile;
    identify the projectile striking the user based on data received from the camera; and
    apply the health modifier to the representation of health to modify the representation of health based on the projectile striking the user.

11. The non-transitory processor-readable medium of claim 10, wherein the outward-facing camera is from a plurality of outward-facing cameras configured to detect motion of the projectile.

12. The non-transitory processor readable medium of claim 10, further comprising code to display a direction of motion of the projectile based on the data received from the outward-facing camera.

13. A system, comprising a processor, the processor configured to:
    receive data captured by at least one outward-facing camera coupled to a personal viewing device, the data including data associated with a beverage bottle captured by the at least one outward-facing camera;
    receive sensor data associated with at least one sensor coupled to the personal viewing device;
    coordinate a display of images based on the data received by the motion capture module, the images representing a simulated environment including the user;
    define a representation of the user's health within the simulated environment;
    identify the user drinking from the beverage bottle based on the data received from the motion capture module and the sensor data capture module; and
    modify the representation of the user's health based on the user drinking from the beverage bottle.

14. The system of claim 13, wherein the processor is configured to coordinate the display of images based on the data received by the motion capture module.

15. The system of claim 13, wherein the personal viewing device is configured to be coupled to a body of a user.

16. The system of claim 13, the at least one outward-facing camera includes an outward-facing motion capture camera and an outward-facing image capture camera.

17. The system of claim 16, wherein:
    the image capture camera is configured to capture an image of the beverage bottle and;
    the processor is configured to cause the display of a representation of the beverage bottle in the display of images, the representation of the beverage bottle being different from the image of the beverage bottle.

* * * * *